(12) United States Patent
Hsieh et al.

(10) Patent No.: US 10,307,461 B2
(45) Date of Patent: Jun. 4, 2019

(54) METHOD OF PREVENTING POLYCYSTIC KIDNEY DISEASE AND PKD ANIMAL MODEL WITH EXOGENOUS NEUTROPHIL GELATINASE-ASSOCIATED LIPOCALIN

(71) Applicant: NATIONAL TAIWAN NORMAL UNIVERSITY, Taipei (TW)

(72) Inventors: Hsiu-Mei Hsieh, Taipei (TW); Yi-Ren Wang, Taipei (TW); Si-Tse Jiang, Taipei (TW); Wen-Yih Jeng, Taipei (TW); Yuan-Yow Chiou, Tainan (TW)

(73) Assignee: NATIONAL TAIWAN NORMAL UNIVERSITY, Taipei (TW)

( * ) Notice: Subject to any disclaimer, the term of this patent is extended or adjusted under 35 U.S.C. 154(b) by 0 days.

(21) Appl. No.: 15/220,687

(22) Filed: Jul. 27, 2016

(65) Prior Publication Data

US 2017/0182120 A1 Jun. 29, 2017

(30) Foreign Application Priority Data

Dec. 23, 2015 (TW) .............................. 104143323 A

(51) Int. Cl.
| | | |
|---|---|---|
| *A61K 38/17* | (2006.01) | |
| *C07K 14/47* | (2006.01) | |
| *A61K 38/16* | (2006.01) | |
| *A01K 67/027* | (2006.01) | |

(52) U.S. Cl.
CPC .......... *A61K 38/1709* (2013.01); *A61K 38/16* (2013.01); *C07K 14/47* (2013.01); *A01K 67/0275* (2013.01); *A01K 67/0276* (2013.01); *A01K 2217/075* (2013.01); *A01K 2227/105* (2013.01); *A01K 2267/0306* (2013.01)

(58) Field of Classification Search
CPC ..... A61K 38/1709; A61K 38/16; C07K 14/47
USPC ..................... 514/15.4, 2; 530/350
See application file for complete search history.

(56) References Cited

U.S. PATENT DOCUMENTS

| | | | |
|---|---|---|---|
| 8,247,376 B2 * | 8/2012 | Barasch ............. | A61K 38/1709 514/15.4 |
| 2008/0090765 A1 | 4/2008 | Schmidt-Ott et al. | |
| 2009/0170143 A1 | 7/2009 | Uttenthal et al. | |
| 2011/0091912 A1 | 4/2011 | Barasch et al. | |
| 2014/0079769 A1 | 3/2014 | Terzi et al. | |

FOREIGN PATENT DOCUMENTS

| | | |
|---|---|---|
| JP | 2007536260 A | 12/2007 |
| WO | WO 2005/107793 A2 | 11/2005 |

OTHER PUBLICATIONS

Wei et al. (2008) Kidney Int., vol. 74(10), 1310-1318.*
Devarajan (2010) Kidney Int., vol. 77, 755-757.*
Feng Wei, et al., "Neutrophil gelatinase-associated lipocalin suppresses cyst growth by Pkd1 null cells in vitro and in vivo", Kidney Int., Nov. 2008, vol. 74, No. 10, pp. 1310-1318.
Rahul D. Pawar, et al., "Neutrophil Gelatinase Associated Lipocalin is Instrumental in the Pathogenesis of Antibody-Mediated Nephritis", Arthritis Rheum., May 2012, vol. 64, No. 5, pp. 1620-1631.
Jaya Mishra et al; "Amelioration of Ischemic Acute Renal Injury by Neutrophil Gelatinase-Associated Lipocalin," Journal of the American Society of Nephrology, vol. 15, p. 3073-3082, Dec. 1, 2004.
Kamura, Koichi, "Polycystic Kidney Disease: Clinical Advances in the Past 10 Years and Topics in 2002," IRYO vol. 57 No. 9, pp. 551-557), 2003.

* cited by examiner

*Primary Examiner* — Anne Marie S Wehbe
(74) *Attorney, Agent, or Firm* — Muncy, Geissler, Olds & Lowe, P.C.

(57) ABSTRACT

Disclosed is a method of treating or preventing polycystic kidney disease (PKD) by administration of neutrophil geleatinase-associated lipocalin (Ngal) protein. Also, a transgenic non-human animal model is established to investigate the effect of overexpression of exogenous Ngal on PKD progression.

5 Claims, 24 Drawing Sheets
(7 of 24 Drawing Sheet(s) Filed in Color)

Specification includes a Sequence Listing.

METHOD OF PREVENTING POLYCYSTIC KIDNEY DISEASE AND PKD ANIMAL MODEL WITH EXOGENOUS NEUTROPHIL GELATINASE-ASSOCIATED LIPOCALIN

CROSS REFERENCE TO RELATED APPLICATIONS

This application claims the benefits of the Taiwan Patent Application Serial Number 104143323, filed on Dec. 23, 2015, the subject matter of which is incorporated herein by reference.

FIELD OF THE INVENTION

The present invention relates to a method of treating or preventing polycystic kidney disease (PKD) and a PKD animal model with exogenous neutrophil gelatinase-associated lipocalin (NGAL).

DESCRIPTION OF RELATED ART

Autosomal dominant polycystic kidney disease (ADPKD) is one of the most common genetic diseases with a prevalence of 1:400 to 1:1000. Mutations in PKD1 on chromosome 16 accounts for approximately 85% of the ADPKD cases (Tones V E, et al., *Lancet*, 369: 1287-1301, 2007; Grantham J J, et al., *Nat Rev Nephrol*, 7: 556-566, 2011). The PKD1 gene encodes polycystin-1 (PC1) and the down-regulation of PC1 is associated with an early cyst formation at embryonic day 15.5 (E15.5) and disease severity in laboratory mice (Piontek K, et al., *Nat Med*, 13: 1490-1495, 2007; Hopp K, et al., *J Clin Invest*, 122: 4257-4273, 2012; Fedeles S V, et al., *Trends Mol Med*, 20: 251-260, 2014; Lu W, et al., *Nat Genet*, 17: 179-181, 1997; Magenheimer B S, et al., *J Am Soc Nephrol*, 17: 3424-3437, 2006).

Patients with ADPKD usually begin to experience symptoms by the age of 40 and progress to renal failure by the age of 50, and require dialysis (such as hemodialysis or peritoneal dialysis) or kidney transplantation to maintain life. ADPKD is inherited as an autosomal dominant trait in families. The phrase "autosomal dominant" means that if one parent has the disease, there is a 50-percent chance that the disease will pass to a child. ADPKD, the fourth leading cause of chronic kidney failure, affects an estimated 12 million people worldwide and six hundred thousand people in the U.S (approximately 1/500 Americans). Approximately 50% of ADPKD patients have renal failure by the age of 50.

Tolvaptan, discovered and developed in Japan by Otsuka Pharmaceutical, was a vasopressin V2-receptor antagonist used to treat hyponatremia (low blood sodium levels) associated with congestive heart failure. The drug was also expected to be effective in the treatment of ADPKD because of its success in animal models using rats and mice. The clinical trials in 1,445 adults with ADPKD have been completed worldwide in support of the ADPKD indication. Tolvaptan has been proven to effectively slow both the increase in total kidney volume and the decline in kidney function in PKD patients. However, a risk of irreversible liver injury was identified in patients with ADPKD taking tolvaptan.

Neutrophil gelatinase-associated lipocalin (NGAL) was a 22-kD secreted lipocalin-family protein and expressed in the nephrons of embryonic kidney. NGAL was involved in kidney development (Yang J, et al., *Mol Cell*, 10: 1045-1056, 2002) and in innate immune response to bacterial infection (Flo T H, et al., *Nature*, 432: 917-921, 2004; Berger T, et al., *Proc Natl Acad Sci*, 103: 1834-1839, 2006). Increased level of NGAL was regarded as an earlier and more sensitive biomarker than creatinine and blood urea nitrogen (BUN) for acute kidney ischemia (AKI) (Mishra J, et al., *J Am Soc Nephrol*, 14: 2534-2543, 2003; Mishra J, et al., *Lancet* 365: 1231-1238, 2005; Urbschat A, et al., *Eur J Clin Invest*, 44: 652-659, 2014; Di Grande A, et al., *Eur Rev Med Pharmacol Sci*, 13: 197-200, 2009; Devarajan P, *Biomark Med*, 8: 217-219, 2014), progression of chronic kidney disease (CKD) (Nickolas T L, et al., *Kidney Int*, 82: 718-722, 2012; Shen S J, et al., *Nephrology (Carlton)*, 19: 129-135, 2014) and severity of PKD (Parikh C R, et al., *Kidney Int*, 81: 784-790, 2012; Meijer E, et al., *Am J Kidney Dis*, 56: 883-895, 2010).

NGAL receptor (NGAL-R, Slc22a17) was expressed in the apical membranes of the distal tubules and collecting ducts and was involved in endocytic iron delivery (Langelueddecke C, et al., *J Biol Chem*, 287: 159-169, 2012). NGAL and NGAL-R coupling contributed to the depletion of intracellular iron, stimulation of apoptosis, and reduction of proliferation (Devireddy L R, et al., *Cell*, 123: 1293-1305, 2005; Schmidt-Ott K M, et al., *J Am Soc Nephrol*, 18: 407-413, 2007 Devarajan P., *Cancer Ther*, 5: 463-470, 2007).

Disclosed in U.S. Patent Publication No. 2014/0079769 A1 is to predict the progression of chronic kidney disease (CKD) by determining the expression level of Ngal gene and to prevent or treat CKD by inhibiting Ngal gene expression. Additionally, U.S. Patent Publication No. 2009/0170143 A1 discloses methods for monitoring or determining the likelihood of a renal disorder by measuring the concentration of NGAL in a sample of bodily fluid from a subject. Further, the method for differentiating between CKD and acute kidney injury or disease (AKI or AKD) is disclosed in U.S. Patent Publication No. 2011/0091912 A1, which relies on detecting the amount of NGAL in the high molecular weight fraction.

U.S. Pat. No. 8,247,376 B2 discloses intravenous, subcutaneous or intraperitoneal administration of NGAL to a patient suffering from ischemic, ischemic-reperfusion, toxin-induced injury, acute or chronic kidney injury. This patent asserts that NGAL can directly target renal proximal tubule cells and enhance the renal re-epithelialization and tubular cell proliferation, and reduce tubule cell apoptosis and high levels of serum or plasma creatinine after ischemia-reperfusion injury.

Although the use of NGAL as therapeutic agents has been disclosed for treatment in patients suffering from ischemic, ischemic-reperfusion, toxin-induced injury, acute or chronic kidney injury, no therapeutic agents or methods without side effects are given for PKD.

SUMMARY OF THE INVENTION

In view of the deficiency of potent anti-PKD drug with no side effect on liver, the inventors of the present invention were devoted to the development of anti-PKD drugs without liver toxicity and thus completed the present invention. In the present invention, PKD mouse model (Pkd1$^{L3/L3}$) and NGAL mouse model (Ngal$^{Tg/Tg}$ with overexpression of kidney-specific NGAL) are established and crossbred to generate Pkd1$^{L3/L3}$; Ngal$^{Tg/Tg}$ mice with PKD and overexpression of NGAL in renal tubules of embryonic kidney and adult kidney. Further, those mouse models can be used to investigate the effect of overexpression of exogenous kidney-specific NGAL on PKD progression. Based on the therapeutic result of overexpressed exogenous kidney-specific NGAL on the prevention or treatment of PKD, a protein medicament for the treatment of PKD can be successfully developed.

The present invention relates to use of neutrophil gelatinase-associated lipocalin (NGAL) in the manufacture of a medicament for the prevention or treatment of polycystic kidney disease (PKD).

The present invention also relates to a method of treating or preventing PKD that includes of a step of administering an effective amount of neutrophil gelatinase-associated lipocalin (NGAL) to a subject with PKD gene mutation. Further, the present invention is directed to a method of genetically treating or preventing PKD in which a foreign gene for overexpression of exogenous NGAL proteins is transferred into a subject with PKD gene mutation by genetic transformation. The subject with PKD gene mutation refers to a subject having a potential for developing PKD, including a potential patient who is not yet ill, but who is susceptible to, or otherwise at risk of, developing PKD, a patient who is progressing towards PKD, and a patient who is diagnosed with PKD. Here, the subject may be a human being or an animal.

Additionally, the present invention establishes $Pkd1^{L3/L3}$; $Ngal^{Tg/Tg}$ mouse model with C57BL/6J genetic background that expresses a low level of full-length PC1 and overexpresses exogenous NGAL. Here, the exogenous Ngal gene can express NGAL under the control of kidney tubular-specific cadherin 16 (Ksp-Cdh16) promoter. The Ngal gene may be any Ngal gene of known organisms which can express fully functional NGAL regardless of whether it is modified. The overexpression of exogenous NGAL is based on rental NGAL/β-actin ratio. For example, the renal level of NGAL in $Pkd1^{L3/L3}$; $Ngal^{Tg/Tg}$ mice is 1.8-fold and 3.7-fold greater than those in $Pkd1^{L3/L3}$ and $Ngal^{Tg/Tg}$ mice, respectively. The low level of PC1 refers to the level of PC1 being 20% or less, particularly to 15% or less and more particularly to 10% or less, of wild type. The animal model can be used to investigate the effect of NGAL or other enzymes, receptors, factors or drugs on PKD.

Furthermore, the lifespan of $Pkd1^{L3/L3}$; $Ngal^{Tg/Tg}$ mice can be 1.6-6 folds, and more particularly to 2-5 folds, longer than that of $Pkd1^{L3/L3}$ mice. The kidney weight to body weight ratio in $Pkd1^{L3/L3}$; $Ngal^{Tg/Tg}$ mice can be 10%-17%, and more particularly to 12.2%-15.5%.

The NGAL can be overexpressed in milk or the eggs of chicken or duck by animal genetic transformation, or in edible components of plants, such as leaves, fruits, seeds, roots or stems, by plant genetic transformation. Alternatively, in the manufacture of NGAL medicament, NGAL expression vector may be transformed into *Escherichia coli* or transfected into CHO cells to produce the NGAL in large quantities, followed by protein purification.

NGAL is versatile in its mode of application, and may be delivered, for example, by oral administration, intravenous injection, intraperitoneal injection or subcutaneous injection. By intravenous injection, NGAL or protein drugs derived therefrom can be delivered into the blood circulatory system and absorbed in kidneys so as to reduce enzymatic degradation or hepatic first-pass effect and maintain efficacy. Additionally, the NGAL or protein drugs derived therefrom in accordance with the present invention is more advantageous than traditional small molecule drug, such as tolvaptan, owing to its high specificity, reduced side effects and toxicity, and high biocompatibility.

The aforementioned PKD includes autosomal dominant polycystic kidney disease (ADPKD) and autosomal recessive polycystic kidney disease (ARPKD). In embodiments of the present invention, the PKD is ADPKD.

The prevention or treatment of PKD refers to preventing, inhibiting, alleviating, treating or ameliorating the disease. In accordance with embodiments of the present invention, the disease is treated by retarding cyst growth, reducing interstitial fibrosis, increasing apoptosis of cystic epithelial cells and decreasing proliferation of cystic epithelial cells in the kidney so as to prolong lifespan of patients. Also, for a subject with PKD gene mutation, the disease can be prevented by administrating exogenous NGAL to the subject having a potential for developing PKD when the subject is not yet ill or is in the embryonic period before the expression of endogenous NGAL.

The delivery of exogenous NGAL to the PKD patients can be realized by genetic transformation for NGAL overexpression or by directly administrating NGAL medicament to patients. NGAL is effective in the prevention or treatment of PKD because it can induce increased active-caspase-3 and reduced α-SMA and hypoxia-inducible factor 1-α (HIF-1α) as well as downregulation of Akt-mTOR-S6K signaling (i.e. reduced proliferating cell nuclear antigen (PCNA), Akt, mammalian target of rapamycin (mTOR) and S6K).

Based on embodiments of the present invention, it can be recognized that NGAL exhibits therapeutic effects in a dose-dependent manner. In other words, for the prevention or treatment of PKD, the level of total NGAL preferably is higher than the level of endogenous NGAL.

BRIEF DESCRIPTION OF THE DRAWINGS

The patent or application file contains at least one drawing executed in color. Copies of this patent or patent application publication with color drawings will be provided by the Office upon request and payment of the necessary fee.

DETAILED DESCRIPTION OF THE PREFERRED EMBODIMENTS

Embodiments

Clinical Human Kidney Specimens and Patients

Figure 1A:
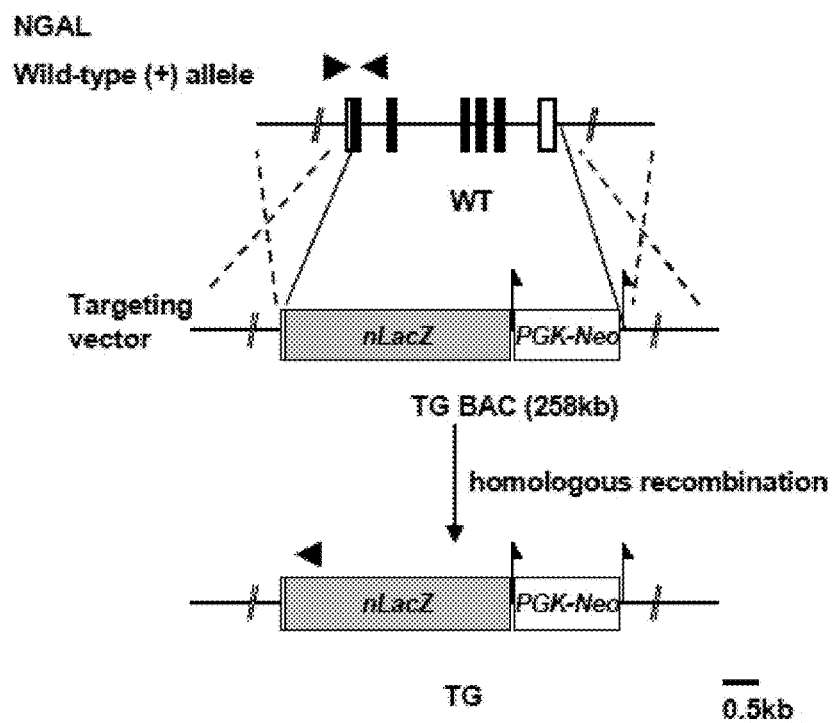
FIGS. 1A-1D show generation of Ngal knockout (KO) and Cdh16-mNgal transgenic (Tg) mice: <FIG. 1A> targeting of the Ngal locus by homologous recombination; <FIG. 1B> schematic map of the Ngal transgene, in which overexpression controlled by a murine Cdh16 kidney-specific promoter; <FIGS. 1C and 1D> PCR-based genotyping of $Ngal^{-/-}$ and $Ngal^{Tg/Tg}$.

All kidney tissues were obtained from the human biobank of National Cheng Kung Hospital. This study was approved by the institutional review board of National Cheng Kung University Medical Center (A-ER-101-228). NGAL protein levels were examined by immunohostochemistry in 3 human kidney specimens (2 PKD cases, 1 normal kidney) obtained from the Department of Pathology, National Cheng Kung University Hospital, Taiwan. Normal tissue was obtained from a deceased patient whose autopsy had confirmed the absence of non-genitourinary tract disease. Case 1 had ADPKD with chronic renal failure due to severe tubulointerstitial nephritis, while case 2 had been diagnosed at 30 weeks of gestational age as premature ARPKD with polycystic mega-kidney, and the pregnancy had been terminated.

Immunohistochemistry

Kidneys were removed and fixed in 10% formalin at 4° C. overnight, then dehydrated and embedded in paraffin, and sectioned at 4 μm for immunostaining. To detect NGAL, kidney sections were blocked with Avidin/Biotin Blocking Kit (Vector Laboratories, Burlingame, Calif.) after deparaffinization and rehydration, and incubated overnight at 4° C. with rabbit anti-NGAL antibody or goat anti-human NGAL antibody. For other immunostaining, a standard immunoperoxidase protocol (Vectastain ABC kit; Vector Laboratories) was used. After blocking with goat serum, sections were incubated with primary antibodies for 1 hour at room temperature, rinsed in PBS, incubated with biotinylated goat anti-rabbit antibodies, rinsed, then incubated with streptavidin-conjugated peroxidase, rinsed, then incubated with 3-amino-9-ethyl-carbazole as a chromogen, counterstained with hematoxylin, and examined by light microscopy.

Animal Experiments

All mice were housed in the National Laboratory Animal Center (NLAC), Tainan, Taiwan, under a 12 h light:dark cycle, and all experiments were conducted according to protocols approved by the Institutional Animal Care and Use Committee of NLAC. In this study, the inventors identified no significant difference between male and female mice prior to experimental execution. Several literatures also conducted their experiments using animals in both sexes. This suggests that the sexes of animals have little impact on the PKD pathological and molecular analyses. Therefore, both sexes of mice were combined and used in the experiments.

PKD Mice

The inventors' previous study described a murine model of PKD. $Pkd1^{L3/L3}$ mice produced low levels of full-length PC1, and progressively developed polycystic kidney disease (Jiang S T, et al., Am J Pathol, 168: 205-220, 2006). The original $Pkd1^{L3/+}$ mice had a mixed C57BL6-129 background and were backcrossed with C57BL/6J mice for more than ten generations to obtain a uniform genetic background. The $Pkd1^{L3/+}$ mice with stable C57BL/6J genetic background were then used to generate the homozygous mutants $Pkd1^{L3/L3}$.

Ngal Knockout Mice

The Ngal conventional knockout mice were generated using VelociGene biotechnology. The murine Ngal gene was disrupted by a PGK/Neo cassette, and lacZ was used as the reporter gene. The $Ngal^{-/-}$ mice were originally bred on a mixed C57BL6-129 background and were backcrossed with C57BL/6J mice for more than ten generations prior to intercrossing to generate $Ngal^{-/-}$, ensuring a uniform genetic background. NGAL conventional knockout can prevent the production of NGAL from kidney and other tissues so as to characterize the renal function of NGAL protein in PKD.

Cdh16-mNgal Transgenic Mice

The Cdh16-mNgal transgenic mice overexpress the murine NGAL under the control of the mouse Cdh16 promoter (Shao X, et al., J Am Soc Nephrol, 13: 1824-1836, 2002). Ksp-Cdh16-mNgal ensured an early expression of exogenous NGAL at a time before the expression of endogenous NGAL and cyst formation in ADPKD. Cdh16-mNgal transgenic mice have a C57BL/6J genetic background. The protocol for DNA recombination was approved by the Institutional Biosafety Committee of the NLAC. Here, the Ngal is NCBI Gene No. 16819 or EMBL-EBI No. ENSMUSG00000026822.

Genotyping

Polymerase chain reaction (PCR) was used to genotype all mutant mice with genomic DNA extracted from the tails. Each sample contained 20 μL of the PCR reaction mixture, and β-actin was used as the internal control. The primer sequences were murine Ngal forward primer sequence, SEQ ID No. 1 (5'-ATGGCCCTGAGTGTCATGTGTC-3'), and murine Ngal reverse primer sequence, SEQ ID No. 2 (5'-GCTCCAGATGCTCCTTGGTATG-3'); and β-actin forward primer sequence, SEQ ID No. 3 (5'-GGCATTGTTAC-CAACTGGGA CG-3'), and β-actin reverse primer sequence, SEQ ID No. 4 (5'-AGG A AGGCTG-GAAAAGAGCC-3'). Ngal knockout mutants were analyzed using the following primers: murine Ngal 5' UTR forward primer sequence, SEQ ID No. 5 (5'-TTCCTCCTC-CAGCACACA TCAGAC-3'), lacZ reverse primer sequence, SEQ ID No. 6 (5'-GAGTAACAACCCGTCG-GATTCTC-3'), and murine Ngal reverse primer sequence, SEQ ID No. 7 (5'-AGGGGTTACTGTC AGAGTGGC-TATC-3').

Western-Blot Analysis

Total proteins (50 μg) extracted from mouse kidneys were subjected to Western-blot analysis. The pQE protein expression system (Qiagen) was used to express mouse full-length NGAL and purified NGAL protein with 6×His-tags. The purified NGAL was then used to generate the NGAL antibody by immunizing the rabbit with mouse full-length NGAL protein. The other antibodies were rabbit polyclonal antibody to Slc22A17 (GTX85032; GeneTex), rabbit polyclonal antibody to GAPDH (631401; BioLegend), mouse monoclonal antibody to α-smooth muscle actin (α-SMA) (A2547; Sigma-Aldrich), rabbit polyclonal antibody to hypoxia-inducible factor 1-α (HIF-1α) (GTX 127309; GeneTex), rabbit monoclonal antibody to mTOR (phospho Ser2448) (5536; Cell Signaling Technology), rabbit monoclonal antibody to mTOR (2983; Cell Signaling Technology), mouse monoclonal antibody to β-actin (8H10D10) (12262; Cell Signaling Technology), rabbit polyclonal antibody to S6K1 (phospho Thr389) (ab2571; Abcam), rabbit monoclonal antibody to p70 S6 Kinase (2708; Cell Signaling Technology), rabbit polyclonal antibody to Akt (phospho Ser473) (9271; Cell Signaling Technology), rabbit polyclonal antibody to Akt (9272; Cell Signaling Technology), rabbit polyclonal antibody to caspase-3 (9662; Cell Signaling Technology), mouse monoclonal antibody to proliferating cell nuclear antigen (PCNA) (307902; Biolegend), rabbit polyclonal antibody to epidermal growth factor receptor (EGFR) (phospho Tyr1068) (2234; Cell Signaling Technology), and rabbit monoclonal antibody to EGFR (GTX61503; GeneTex).

Histology and Histomorphometric Analyses

Specimens were fixed in formalin, embedded in paraffin, cut into 4 sections, and stained with hematoxylin and eosin (H&E) or Masson's trichrome for examination by light microscopy (Eclipse E600 Nikon, Japan), as described previously (Wang, E. et al., J Pathol, 222: 238-248, 2010). Quantification of cyst number and size (H&E staining) and staining of collagen fiber (Masson's trichrome) was performed by who was blinded to the mouse genotypes. The Image-Pro Plus v. 4.5.0.29 software (Media Cybernetics, Rockville, Md., 20850 USA) was used to calculate mean quick scores (QSs). For each slide, the software randomly selected five fields (200×) for analysis. After adequate white balance, the software allows the operator to gate areas of special interest and to examine them separately by grabbing digital images. Each slide was analyzed to determine the label index (LI; ratio of positively stained areas to the total area) and the mean optical density (MOD; stain concentration, based on counts of positive pixels). The QS was calculated as the mathematical product of LI and MOD. For counting of cysts, representative images of H&E-stained transverse kidney sections, including the cortex, medulla, and papilla, were used. A grid was placed over the images, and the percentage of grid intersection points that bisected cystic and non-cystic areas was calculated.

Statistical Analysis

Comparisons were made among three groups: $Pkd1^{L3/L3}$, $Pkd1^{L3/L3}; Ngal^{Tg/Tg}$, and $Pkd1^{L3/L3}; Ngal^{-/-}$. Parametric data were compared all groups with one-way ANOVA, and followed with Tukey multiple comparison tests of every pair. Due to the non-normal distributions, survival times are presented as medians and interquartile ranges (25%-75%), and groups were compared by the non-parametric Kruskal-Wallis test with Dunn's multiple comparisons test. Survival curves were constructed, and Kaplan-Meier estimates were used to compare survival rates of the different groups using the log-rank test. A p-value less than 0.05 was considered statistically significant.

<Results>

Generation of Ngal Conventional Knockout and Cdh16-mNgal Transgenic Mice

Figure 1B:
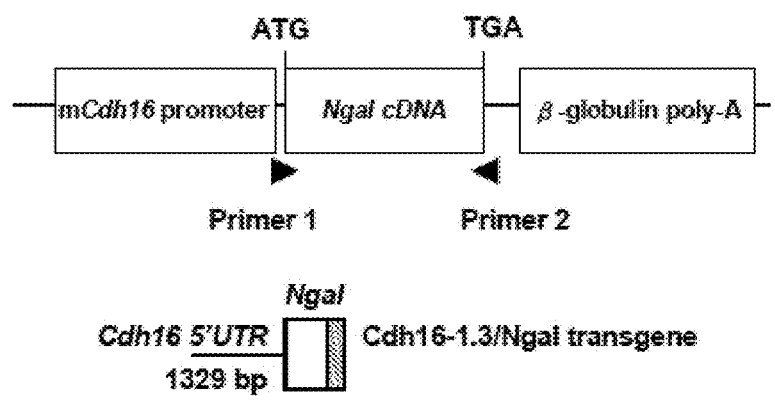
Figure 1C:
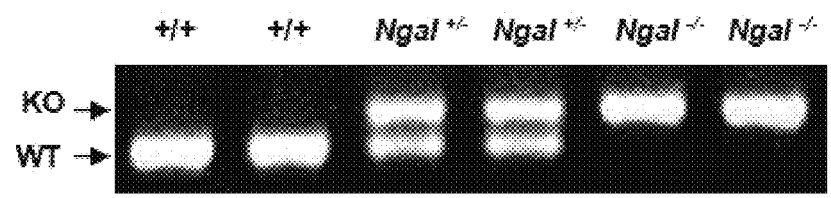
Figure 1D:
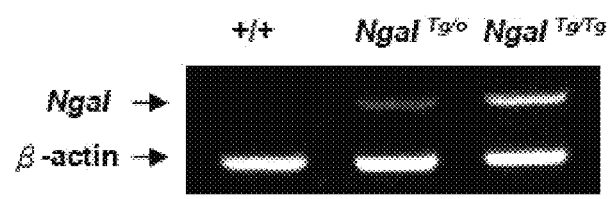
Figure 2A:
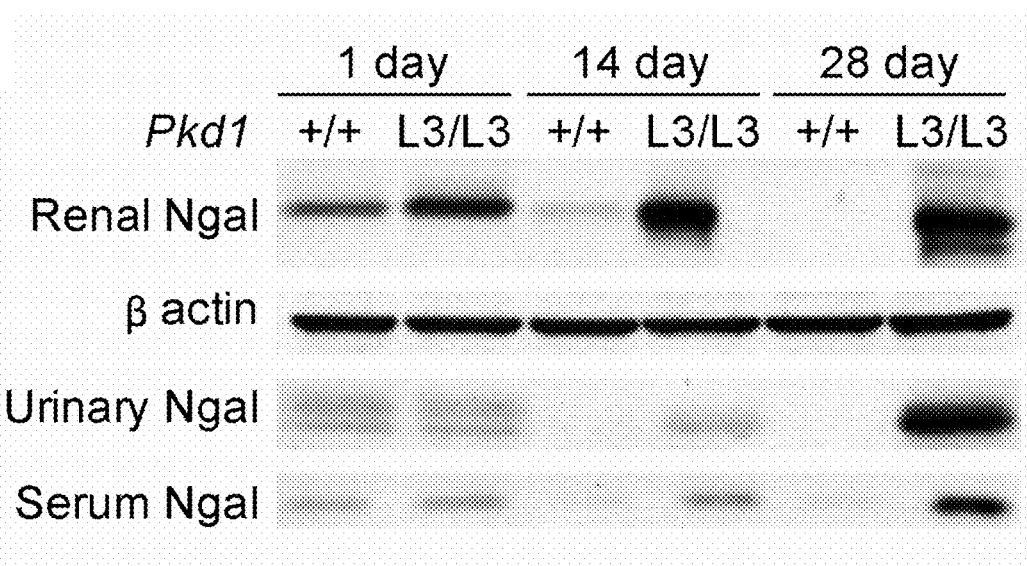
FIGS. 2A-2D show temporal expression of NGAL in kidneys of $Pkd1^{L3/L3}$ and wild-type mice identified by Western-blot analyses: <FIG. 2A> western blotting results of NGAL expression in kidneys, urine, and serum of $Pkd1^{L3/L3}$ and wild-type mice; <FIGS. 2B, 2C and 2D> quantitation of western blot, in which β-actin was used as loading control, and data are means±SEM; n=6; *p<0.05;  p≤0.01;* p≤0.001)
Figure 2B:
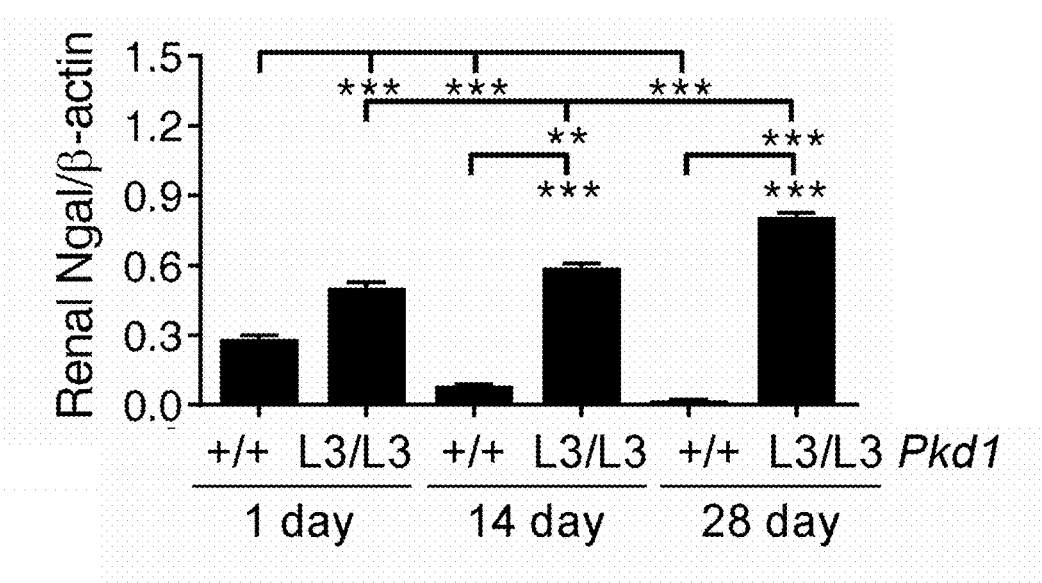
Figure 2C:
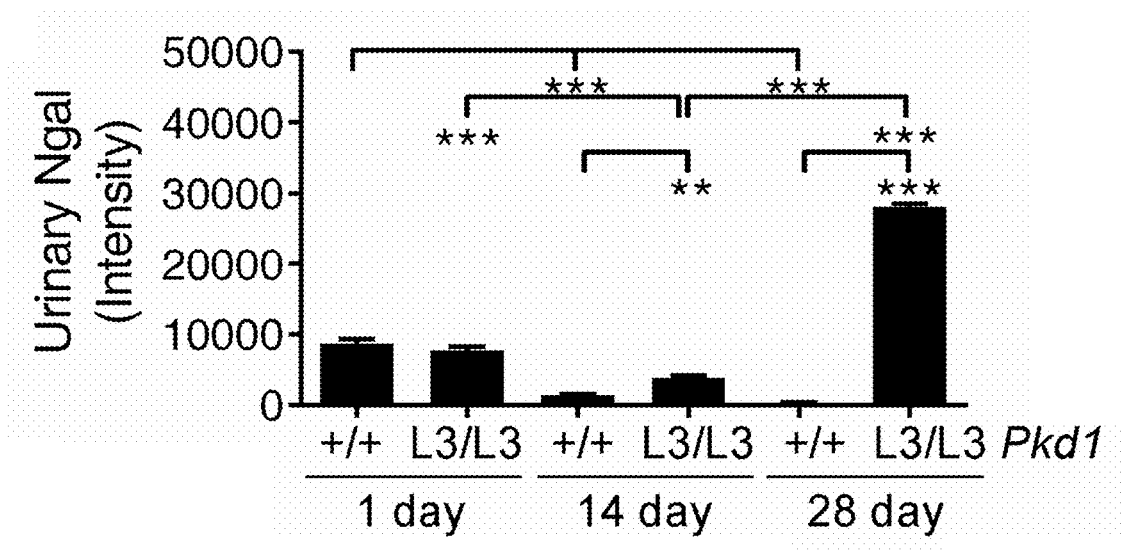
Figure 2D:
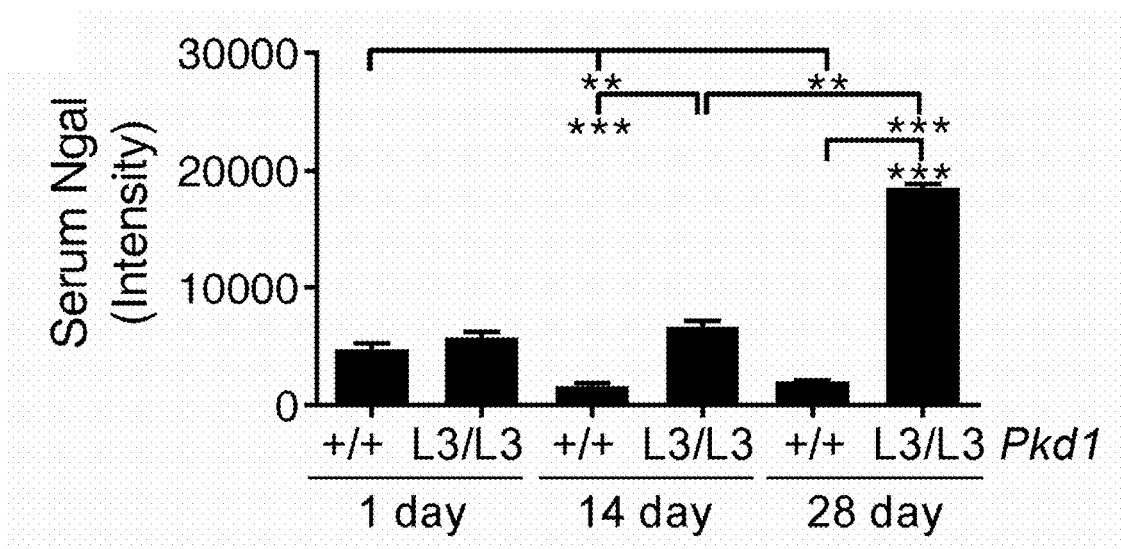

The mouse Ngal targeting strategy and construction of the Cdh16-mNgal transgene were shown in FIGS. 1A and 1B, respectively. PCR analysis confirmed the genotyping of these mice (FIG. 1C). The ratio of the heterozygous $Ngal^{Tg/o}$ mice also confirmed the homozygosity of the $Ngal^{Tg/Tg}$ mice after backcrossing with wild type C57BL/6J mice. The expression level of Ngal was positively correlated with the copy number of Ngal in $Ngal^{Tg/o}$ and $Ngal^{Tg/Tg}$ mice (FIG. 1D).

Figure 3:
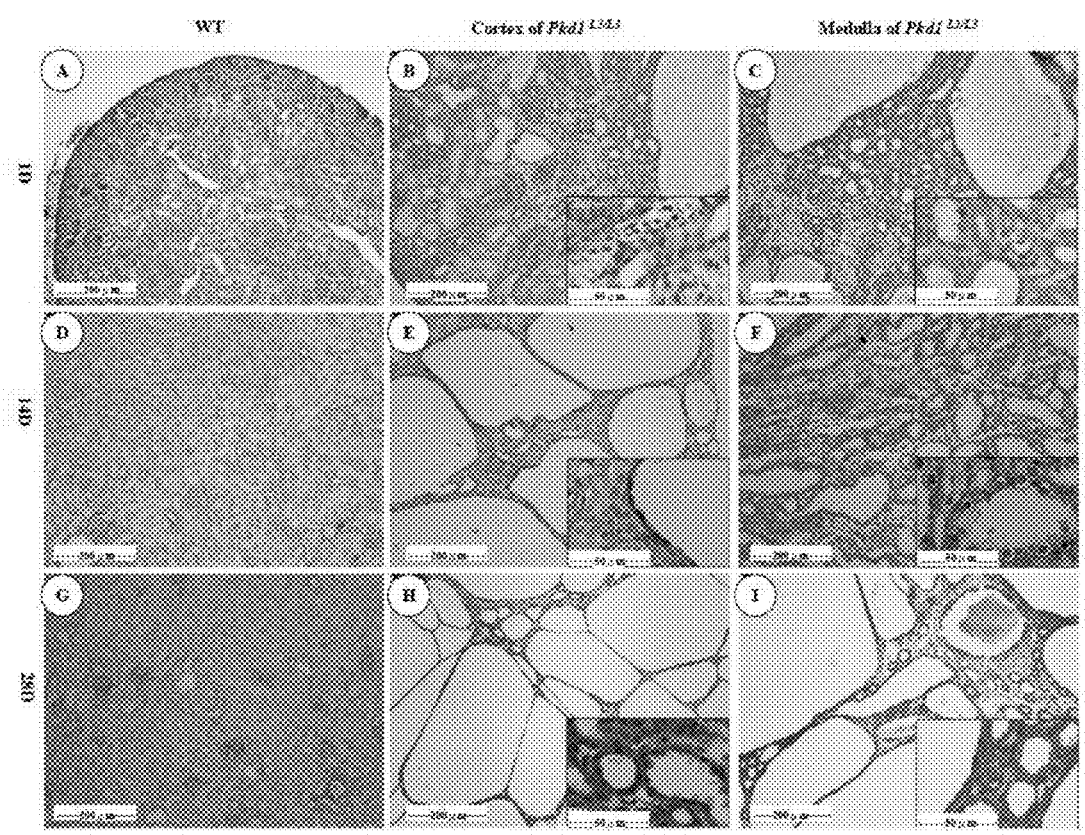
FIG. 3 shows temporal expression of NGAL in kidneys of $Pkd1^{L3/L3}$ and wild-type mice identified by immunohistochemical analysis, in which renal sections at different ages of wild-type and homozygous kidneys were stained with NGAL antibody: (A-C) on day 1 (1D) of renal section, brown staining of NGAL was apparent in medulla but not in glomerulus and cortical tubules in wild-type (WT) mice (A), and in part of the renal cortex (B) and medulla (C) in $Pkd1^{L3/L3}$ mice; (D-F) on 14D of renal section, the expression of NGAL was decreased than 1D in wild-type mice (D), but increased than 1D in the renal cortex (E) and medulla (F) in $Pkd1^{L3/L3}$ mice; (G-I) on 28D of renal section, cyst enlargement was greater than 14D (E, F) in $Pkd1^{L3/L3}$ mice, in which (i) cuboidal epithelium transformed into a squamous pattern during cyst enlargement, and expression of NGAL was also found (E, F, H, I), (ii) all images are representative of at least three mice per genotype in two independent experiments, and (iii) bars=200 µm figures (A-I) and 50 µm in insets (B, C, E, F, H, I)
Figure 4:
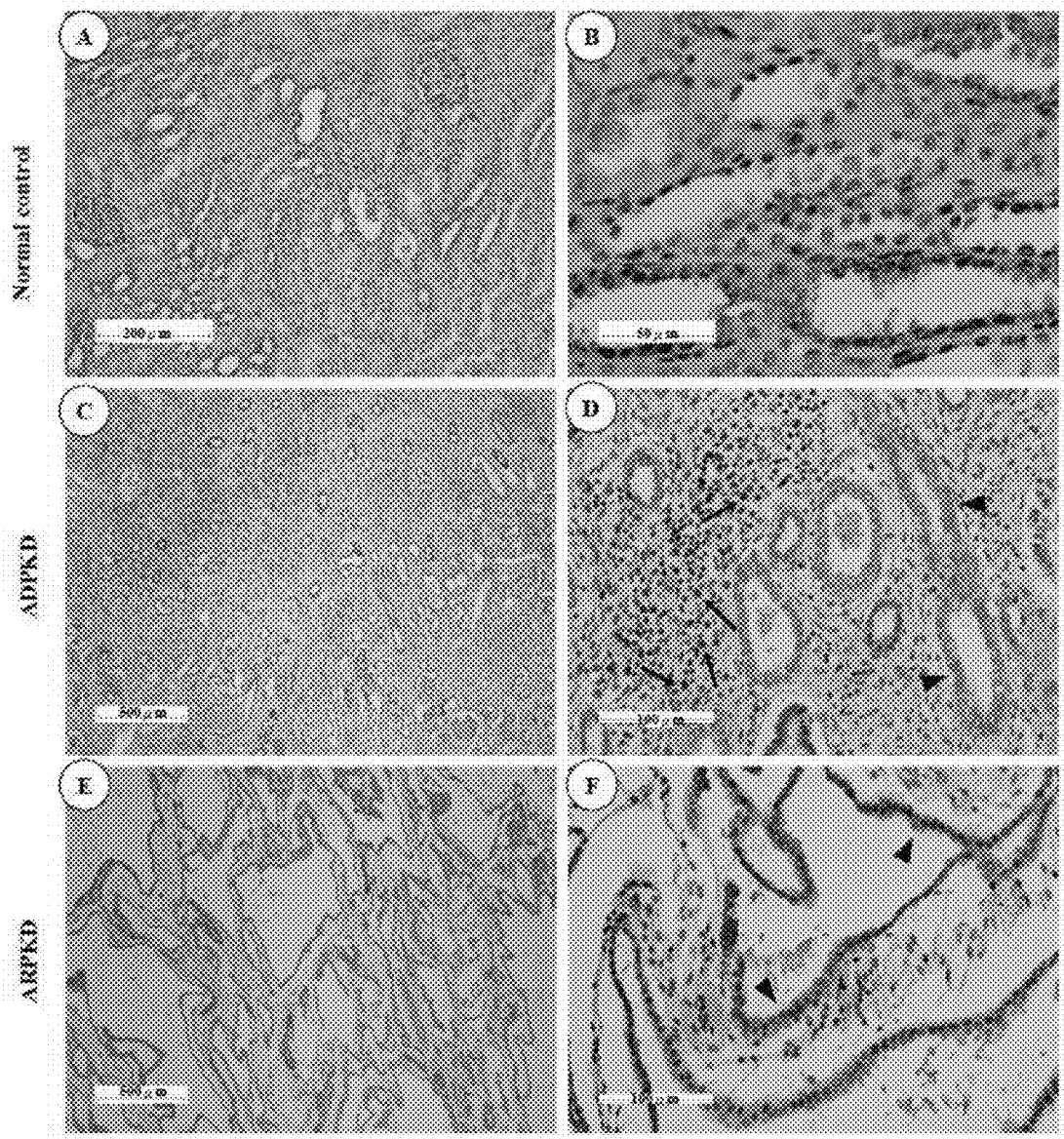
FIG. 4 shows NGAL expression in renal tissue of patients with ADPKD and ARPKD: NGAL expression in human renal tissues of normal (A, B), ADPKD (C, D), and ARPKD (E, F), in which (i) the arrowheads indicate dark brown staining for NGAL in both ADPKD and ARPKD sections, (ii) the arrows indicate staining of endogenous NGAL expression in mononuclear cells in the interstitium area of ADPKD section, and (iii) bars=200 µm (A), 50 µm (B), 500 µm (C, E), and 100 µm (D, F)
Figure 5A:
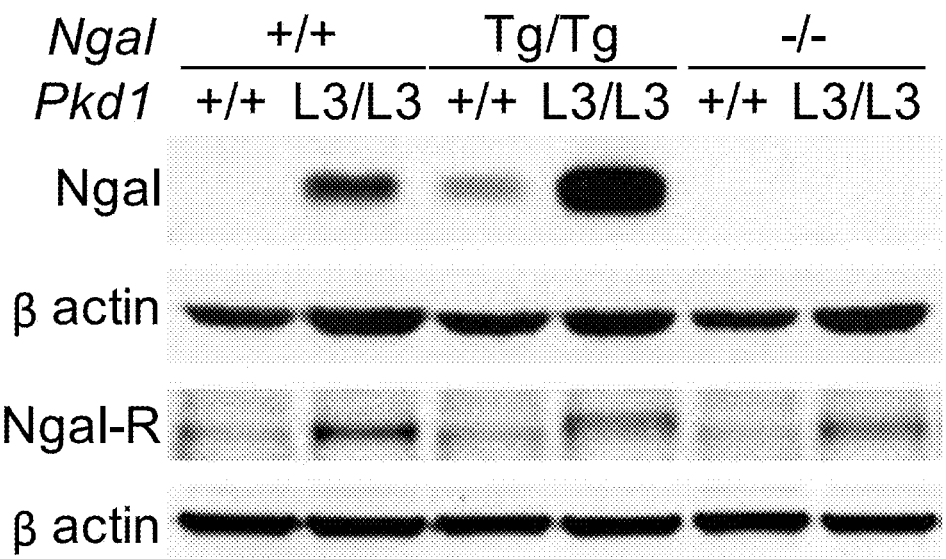
FIGS. 5A-5C show that the renal level of Ngal is greater in $Pkd1^{L3/L3}$; $Ngal^{Tg/Tg}$ mice than in $Pkd1^{L3/L3}$ and $Ngal^{Tg/Tg}$ mice: <FIG. 5A> representative Western blotting of NGAL, NGAL-R, and β-actin (control) at 21 days after birth (21D) in the mice with different genotypes; <FIGS. 5B and 5C> quantification of Western blotting results for NGAL and NGAL-R, in which bars show the means±standard errors of the means (SEM) of three individual mice; *** p<0.001.
Figure 5B:
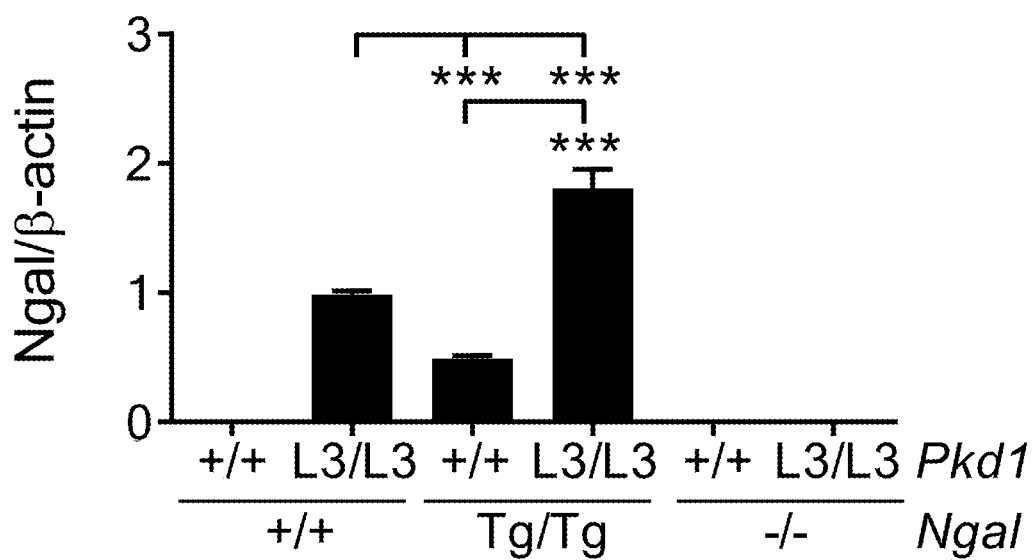
Figure 5C:
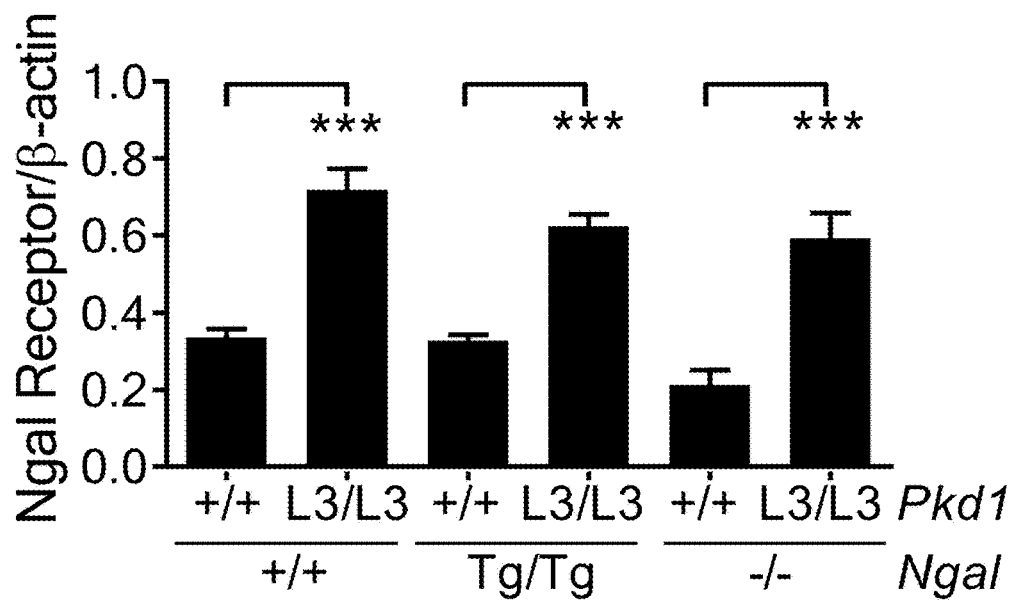

The Level of NGAL is Increased in the Kidneys of $Pkd1^{L3/L3}; Ngal^{Tg/Tg}$ Mice $Pkd1^{L3/L3}; Ngal^{Tg/Tg}$ mice were generated by crossbreeding $Pkd1^{L3/+}; Ngal^{Tg/Tg}$ mice with $Pkd1^{L3/+}; Ngal^{Tg/Tg}$ mice. Western-blot analysis detected the differential expression of endogenous NGAL in urine, serum and kidneys of $Pkd1^{L3/L3}$ and wild type mice (FIGS. 2A-2D). The level was gradually increased along the course of cyst enlargement in $Pkd1^{L3/L3}$ mice; whereas its level was decreased with age in wild type mice. Immunohistochemical analysis revealed a temporal expression pattern of renal NGAL at 1 day (D), 14D and 28D of age in both wild type and $Pkd1^{L3/L3}$ mice (FIG. 3). Endogenous NGAL was mainly localized at the apical surface of cystic epithelia in $Pkd1^{L3/L3}$ mice at 14D and 28D, and cysts were enlarged with age in the renal medulla in $Pkd1^{L3/L3}$ mice. Similar patterns were observed as well in the kidneys of patients with ADPKD or autosomal recessive polycystic kidney disease (ARPKD) (FIG. 4). The results indicated that an upregulation of endogenous NGAL in cystic epithelia might represent an abnormal renal development, and this argument is supported by the role of NGAL in the severity of PKD. The renal expression of NGAL and NGAL-R in these three PKD mice (namely $Pkd1^{L3/L3}$ mice, $Pkd1^{L3/L3}; Ngal^{Tg/Tg}$ mice, $Pkd1^{L3/L3}; Ngal^{-/-}$ mice) at 21D was next examined by Western-blot analysis (FIG. 5A). The renal level of NGAL in $Pkd1^{L3/L3}; Ngal^{Tg/Tg}$ mice was 1.8-fold and 3.7-fold greater than thoses in the $Pkd1^{L3/L3}$ and $Ngal^{Tg/Tg}$ mice, respectively (FIG. 5B). In addition, the renal expression of NGAL-R in these three PKD mice was significantly upregulated as compared to those in the control littermates without PKD (p<0.001) (FIGS. 5A and 5C). The results demonstrated that exogenous NGAL is continuously overexpressed in the embryonic kidney under the control of Ksp-Cdh16 promoter before the expression of endogenous NGAL, and this suggests that exogenous NGAL can prevent progression of PKD in $Pkd1^{L3/L3}$ mice at embryonic stage.

Figure 6A:
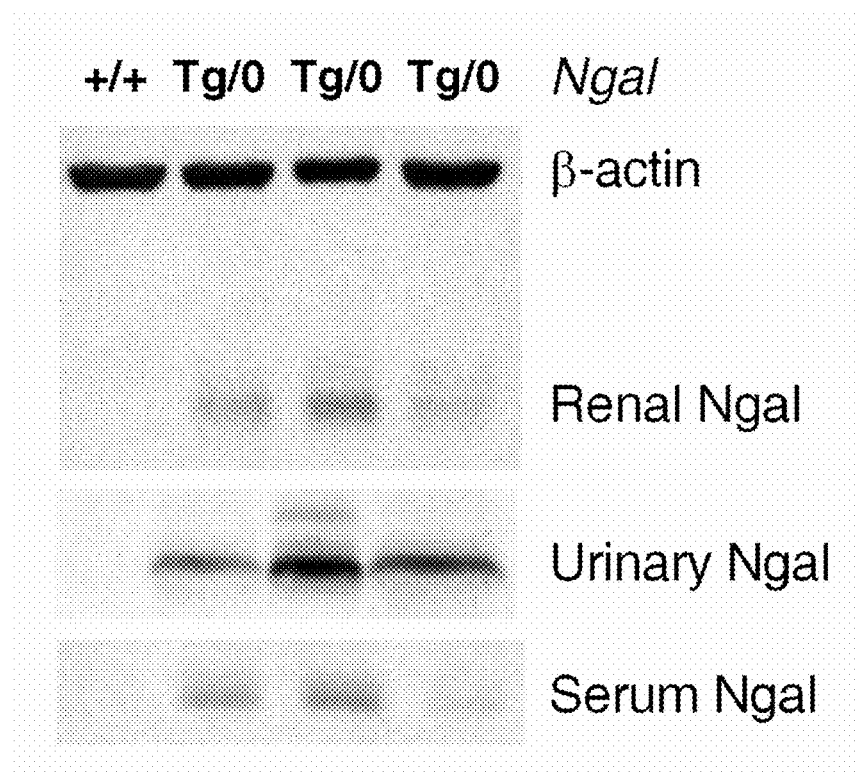
FIGS. 6A-6F show expression of NGAL in kidney, urine, and serum of $Ngal^{Tg/0}$ mice, expression of NGAL in major organs of different mice, and glomerulus number in kidney sections of $Ngal^{Tg/Tg}$ and $Ngal^{-/-}$ mice as compared with wild type mice: <FIG. 6A> western blotting results of NGAL expression in kidneys, urine, and serum of $Ngal^{Tg/0}$ mice; <FIGS. 6B, 6C, 6D and 6E> western blotting results of NGAL expression in the major organs of wild type, $Ngal^{-/-}$, $Ngal^{Tg/Tg}$, and $Pkd1^{L3/L3}$; $Ngal^{Tg/Tg}$ mice, in which the cystic fluid was as a positive loading control (+); <FIG. 6F> the number of renal glomeruli of 21-day-old- and sex-matched in wild type (filled circle), $Ngal^{Tg/Tg}$ (filled square), and $Ngal^{-/-}$ (filled triangle) mice by Kruskal-Wallis test, in which all results represent the median with interquartile range (25%-75%)
Figure 6B:
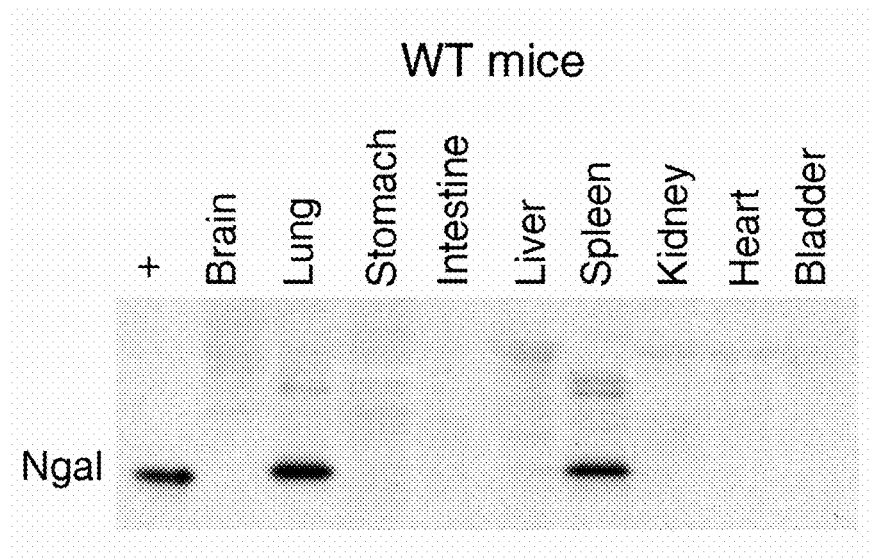
Figure 6C:
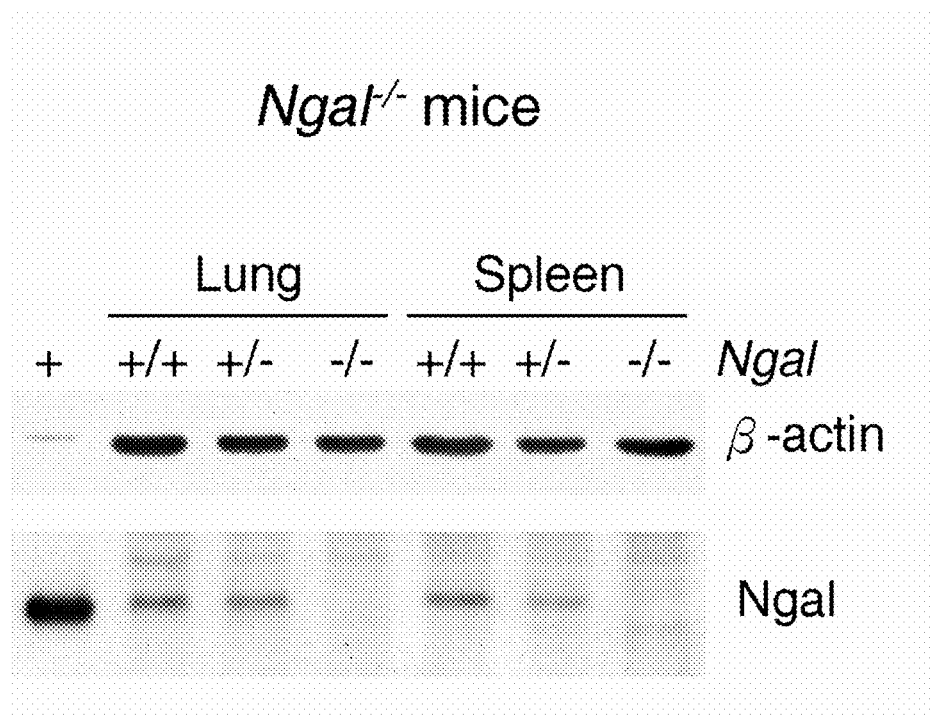
Figure 6D:
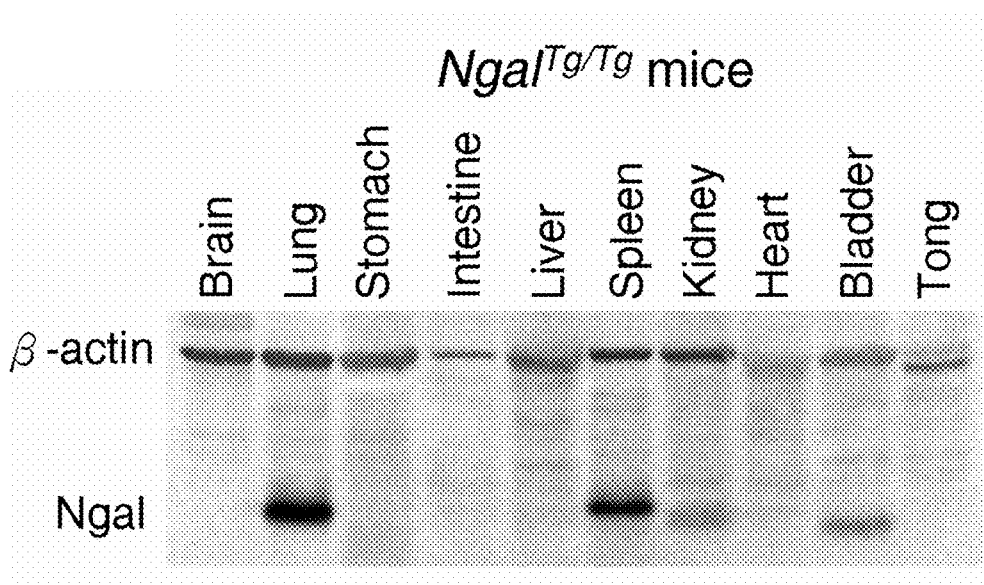
Figure 6E:
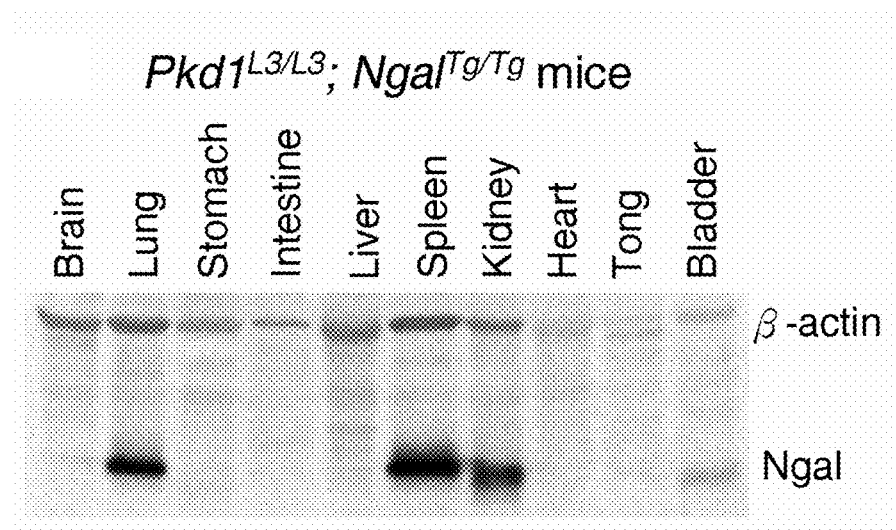
Figure 6F:
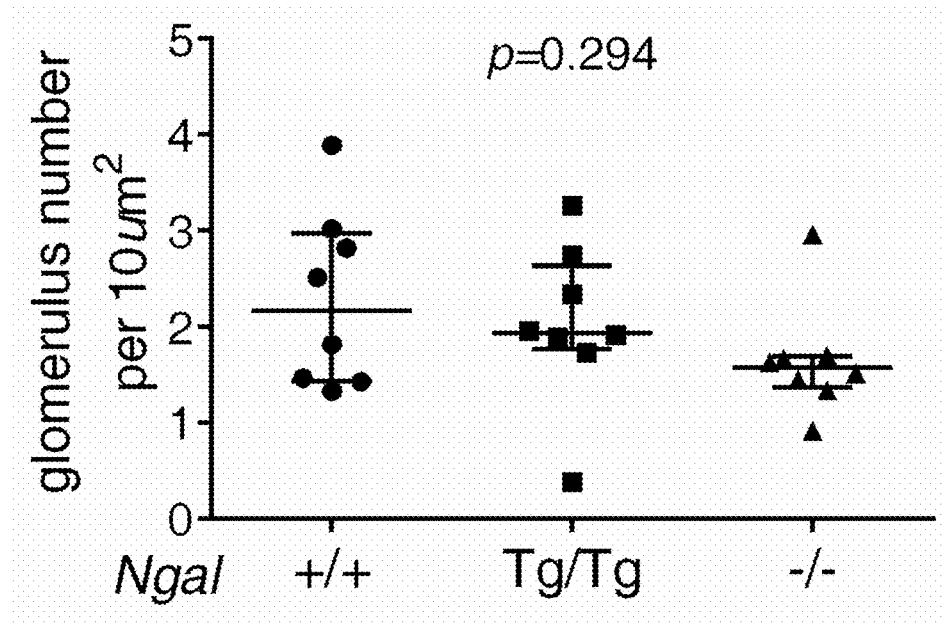

Kidney-Specific Overexpression of Exogenous NGAL in $Ngal^{Tg/Tg}$ and $Pkd1^{L3/L3}; Ngal^{Tg/Tg}$ Mice Western-blot analysis detected the expression of exogenous NGAL in urine, serum and kidneys of $Ngal^{Tg/o}$ mice (FIG. 6A). Comparing wild type and $Ngal^{-/-}$ mice, it was observed that NGAL was expressed in the tissue of lung and spleen in wild type (WT) mice (FIG. 6B) but not seen in $Ngal^{-/-}$ mice (FIG. 6C). Additionally, the kidney-specific overexpression of exogenous NGAL was detected in $Ngal^{Tg/Tg}$ (FIG. 6D), and $Pkd1^{L3/L3}; Ngal^{Tg/Tg}$ (FIG. 6E) mice. Furthermore, the effects of NGAL on the renal development was examined by counting glomeruli in the kidney sections of $Ngal^{Tg/Tg}$ mice and $Ngal^{-/-}$ mice as compared with wild type mice (FIG. 6F). These results showed that the number of renal glomeruli had no significant differences among these age- and sex-matched mice (p=0.294).

Figure 7A:
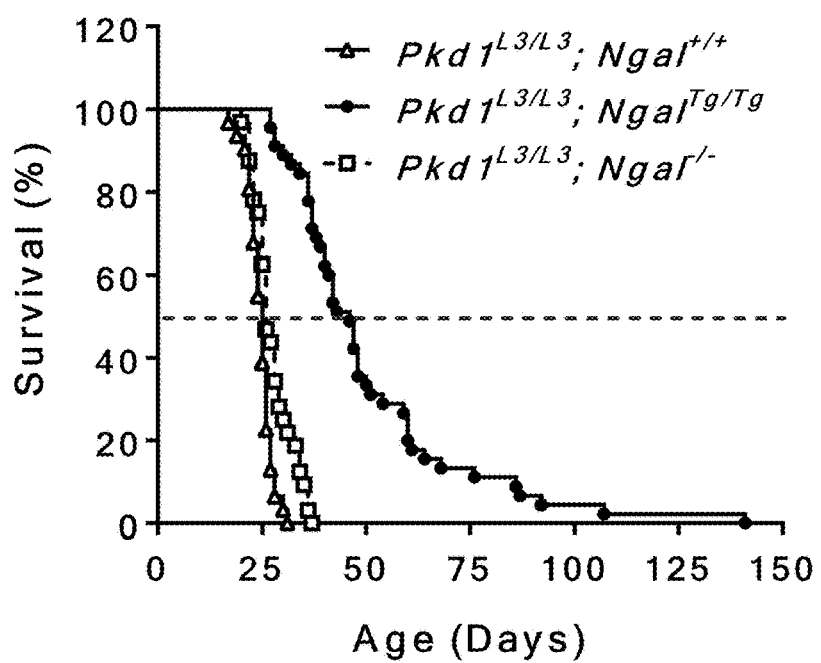
FIGS. 7A-7B show that the overexpression of exogenous kidney-specific NGAL prolongs the survival of $Pkd1^{L3/L3}$ mice: <FIG. 7A> Kaplan-Meier analysis of survival in $Pkd1^{L3/L3}$ (open triangles), $Pkd1^{L3/L3}$; $Ngal^{Tg/Tg}$ (filled circles), and $Pkd1^{L3/L3}$; $Ngal^{-/-}$ (open squares) mice, in which the log-rank test showed significant differences between $Pkd1^{L3/L3}$; $Ngal^{Tg/Tg}$ and $Pkd1^{L3/L3}$ mice, and between $Pkd1^{L3/L3}$; $Ngal^{Tg/Tg}$ and $Pkd1^{L3/L3}$; $Ngal^{-/-}$ mice (both p<0.001); <FIG. 7B> the median survival days in $Pkd1^{L3/L3}$ (n=31, median=25 days), $Pkd1^{L3/L3}$; $Ngal^{Tg/Tg}$ (n=45, 46 days), and $Pkd1^{L3/L3}$; $Ngal^{-/-}$ (n=32, 26 days) mice, in which all results represent the median with interquartile range (25%-75%); *** p<0.001.
Figure 7B:
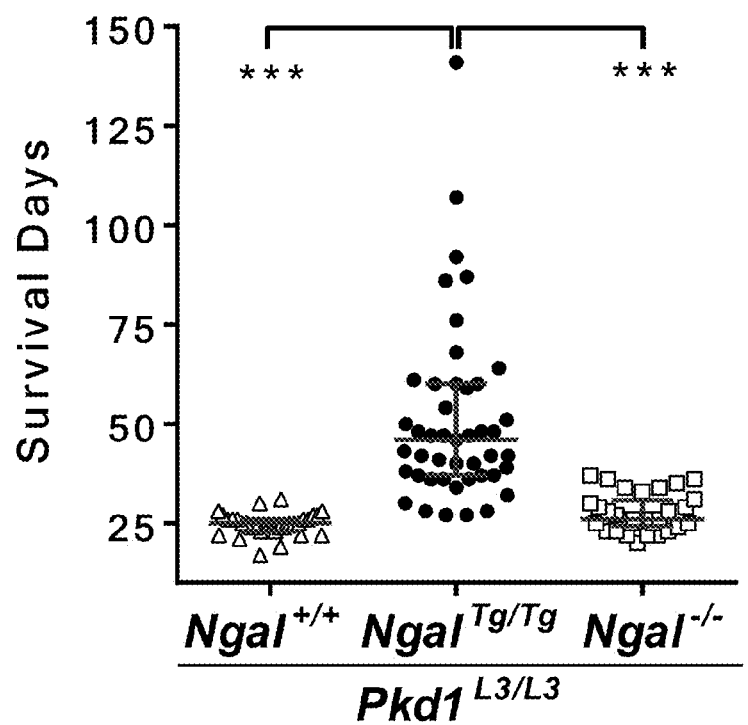

Overexpression of Cdh16-mNgal Prolongs the Survival of $Pkd1^{L3/L3}; Ngal^{Tg/Tg}$ Mice By the differential expression of NGAL, the effect of NGAL on the survival of $Pkd1^{L3/L3}$, $Pkd1^{L3/L3}; Ngal^{Tg/Tg}$ and $Pkd1^{L3/L3}; Ngal^{-/-}$ mice can be observed (FIG. 7A). The log-rank tests showed that the lifespan of $Pkd1^{L3/L3}; Ngal^{Tg/Tg}$ mice was a significantly longer (median=46 days, Interquartile-Range [IQR] 37-60 days) than those of $Pkd1^{L3/L3}$ (25 days, IQR 23-26 days) and $Pkd1^{L3/L3}; Ngal^{-/-}$ mice (26 days, IQR 24-31 days) (both p<0.001 versus $Pkd1^{L3/L3}; Ngal^{Tg/Tg}$ mice) (FIG. 7B). Additionally, there was no significant difference between the lifespan of $Pkd1^{L3/L3}$ and $Pkd1^{L343}; Ngal^{-/-}$ mice (p=0.2988).

Figure 8A:
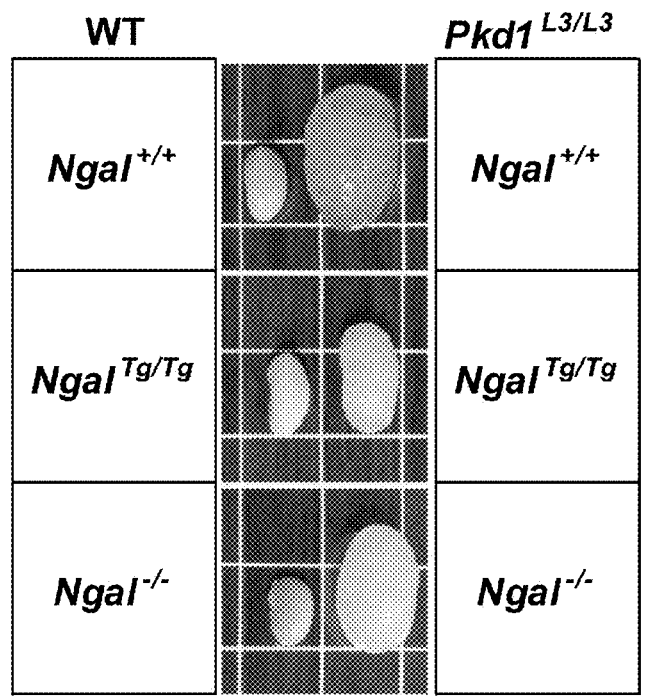
FIGS. 8A-8D show that the overexpression of exogenous kidney-specific NGAL reduces the renal cysts of $Pkd1^{L3/L3}$ mice: <FIG. 8A> representative images of the kidneys of each genotype; <FIG. 8B> the median percentage of kidney weight to body weight in $Pkd1^{L3/L3}$ (n=10, median=23.1%), $Pkd1^{L3/L3}$; $Ngal^{Tg/Tg}$ (n=9, 14.1%), and $Pkd1^{L3/L3}$; $Ngal^{-/-}$ (n=9, 24.4%) mice at 21D by Dunn's multiple comparisons test; <FIG. 8C> the size of renal cysts in $Pkd1^{L3/L3}$ (430.1 µm²), $Pkd1^{L3/L3}$; $Ngal^{Tg/Tg}$ (124.0 µm²), and $Pkd1^{L3/L3}$; $Ngal^{-/-}$ (339.8 µm²) mice; <FIG. 8D> the number of renal cysts, in which all results represent the median with interquartile range (25%-75%); *** p<0.001.
Figure 8B:
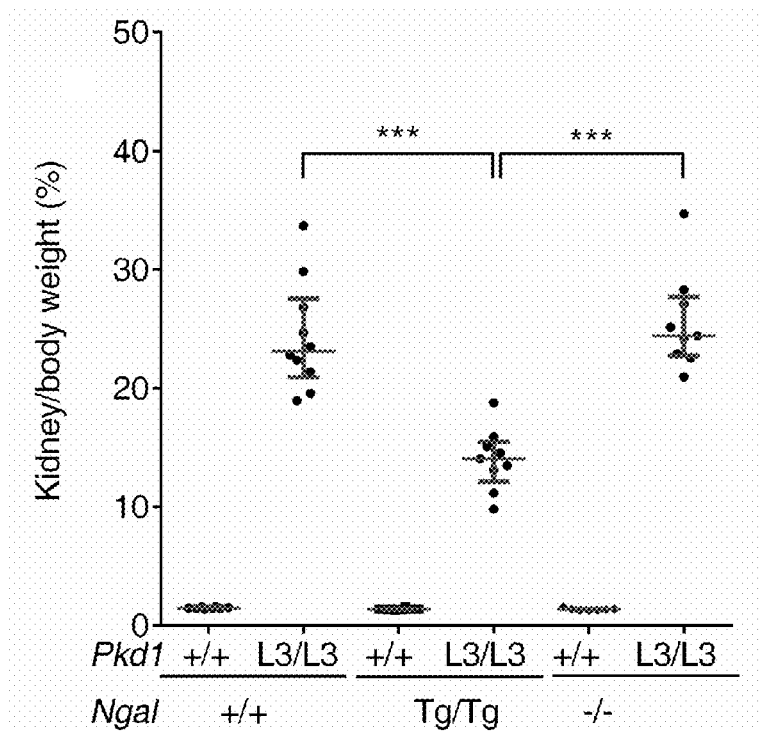
Figures 8C, 8D:
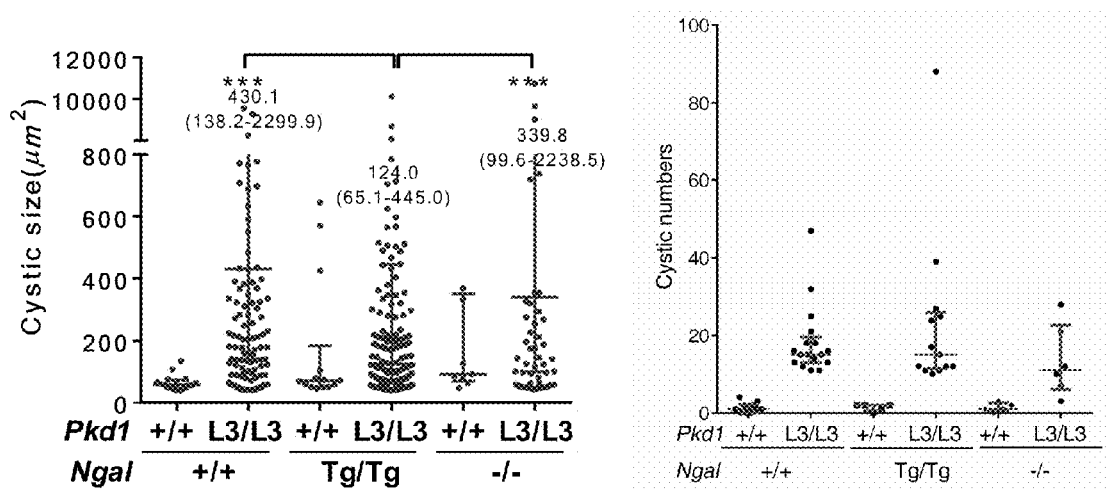

Overexpression of Cdh16-mNgal Retards Cyst Enlargement in $Pkd1^{L3/L3}; Ngal^{Tg/Tg}$ Mice The total kidney volume (TKV) was known to be positively correlated with increased BUN and disease progression of PKD. Polycystic kidneys progressed to the terminal stage at 21D in $Pkd1^{L3/L3}$ and $Pkd1^{L3/L3}; Ngal^{-/-}$ mice. The kidneys of $Pkd1^{L3/L3}; Ngal^{Tg/Tg}$ mice were smaller than those of $Pkd1^{L3/L3}$ and $Pkd1^{L3/L3}; Ngal^{-/-}$ mice (FIG. 8A). Additionally, the median kidney weight to body weight ratio at 21D was significantly lower in $Pkd1^{L3/L3}; Ngal^{Tg/Tg}$ (median=14.1%, IQR 12.2-15.5%) than in $Pkd1^{L3/L3}$ (23.1%, IQR 20.9-27.6%) and $Pkd1^{L3/L3}; Ngal^{-/-}$ (24.4%, IQR 22.7-27.7%) mice (both p<0.001 versus $Pkd1^{L3/L3}; Ngal^{Tg/Tg}$) (FIG. 8B). Renal cyst size was also significantly smaller in $Pkd1^{L3/L3}; Ngal^{Tg/Tg}$ mice than in other two kinds of PKD mice (both p<0.001 versus $Pkd1^{L3/L3}; Ngal^{Tg/Tg}$) (FIG. 8C), whereas there was no significant difference in cyst numbers (FIG. 8D). These results demonstrated that overexpression of exogenous kidney-specific NGAL could prevent rapid progression of PKD by reducing cyst size but not cyst number of $Pkd1^{L3/L3}$ mice. Based on the results, it can be recognized that the deletion of Ngal has no effect on PKD possible, which suggests that the decreased PC1 but not NGAL determines the PKD progression. Additionally, upregulation of endogenous NGAL of $Pkd1^{L3/L3}$ mice cannot protect mice from early death.

Figure 9A:
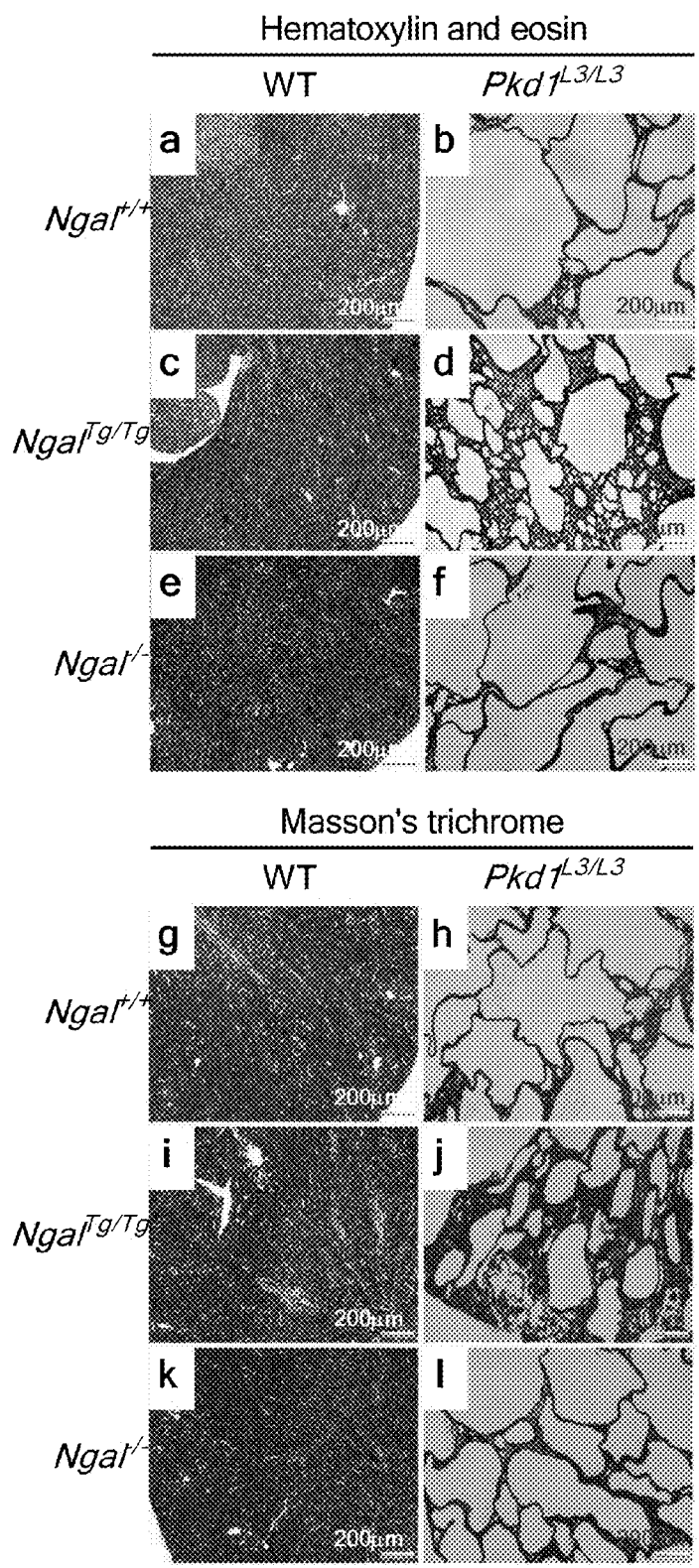
FIGS. 9A-9E show that the overexpression of exogenous kidney-specific NGAL reduces the interstitial fibrosis of $Pkd1^{L3/L3}$ mice: <FIG. 9A> hematoxylin and eosin staining (upper) and Masson's trichrome staining (lower, scale bar: 200 µm; <FIG. 9B> renal fibrosis scores, determined from Masson's trichrome-stained kidneys and calculated as described in the embodiments, in which all results represent the median with interquartile range (25%-75%); <FIG. 9C-9E> representative Western blotting and quantification of results for α-SMA and HIF-la, in which bar charts show means±SEM of three samples; *p<0.05; p<0.01; *p<0.001.
Figure 9B:
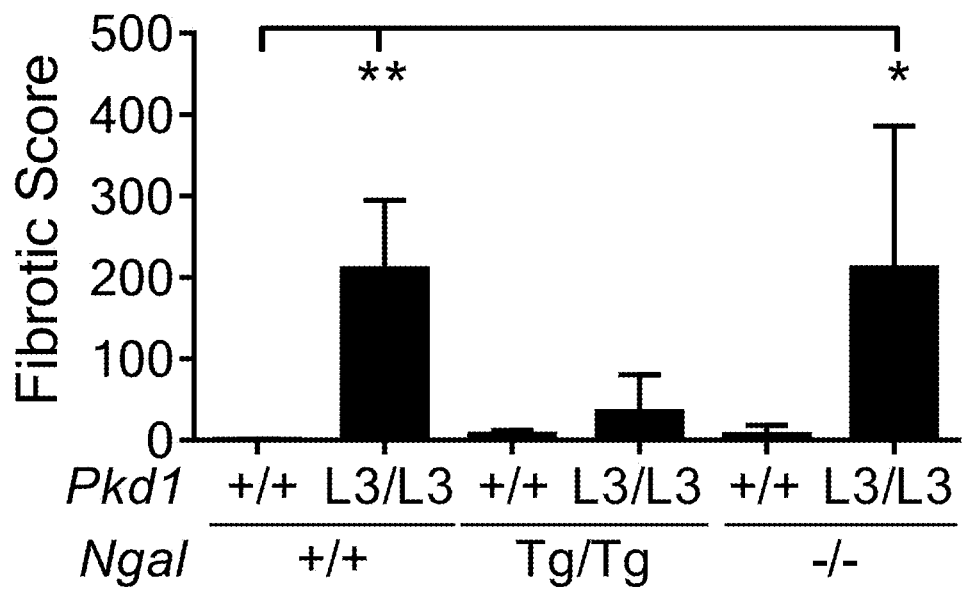
Figure 9C:
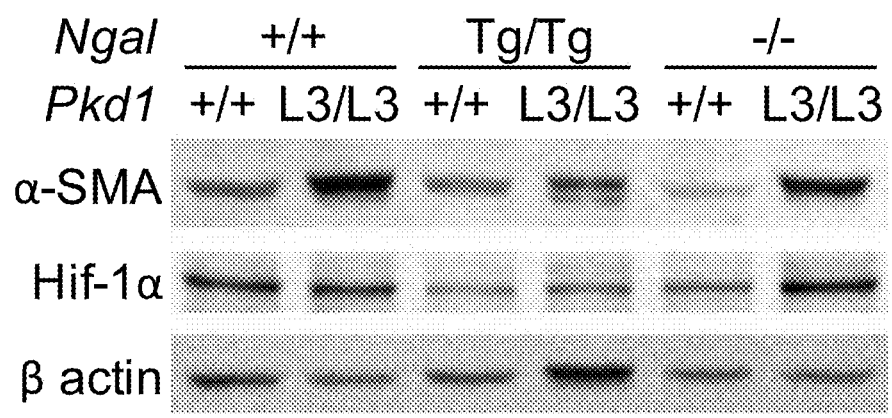
Figure 9D:
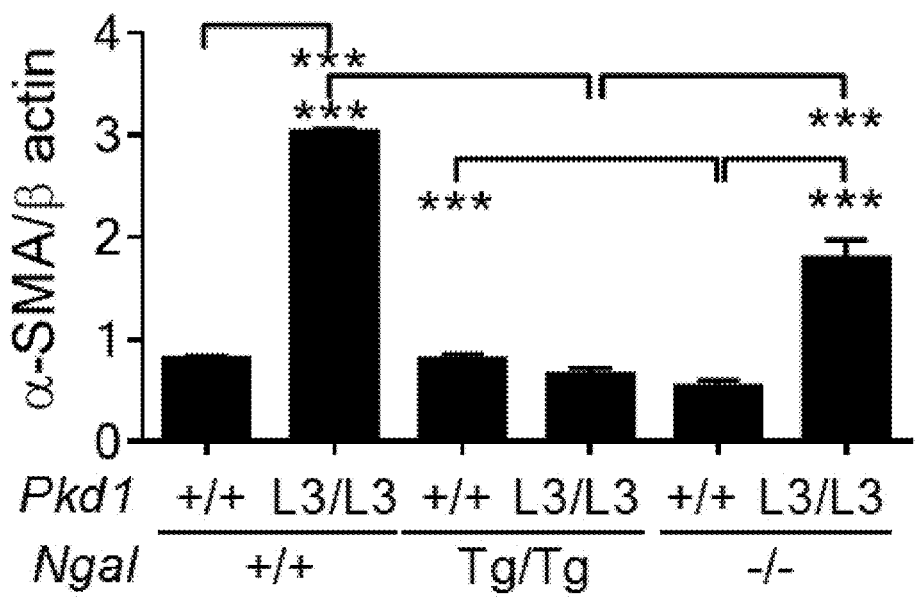
Figure 9E:
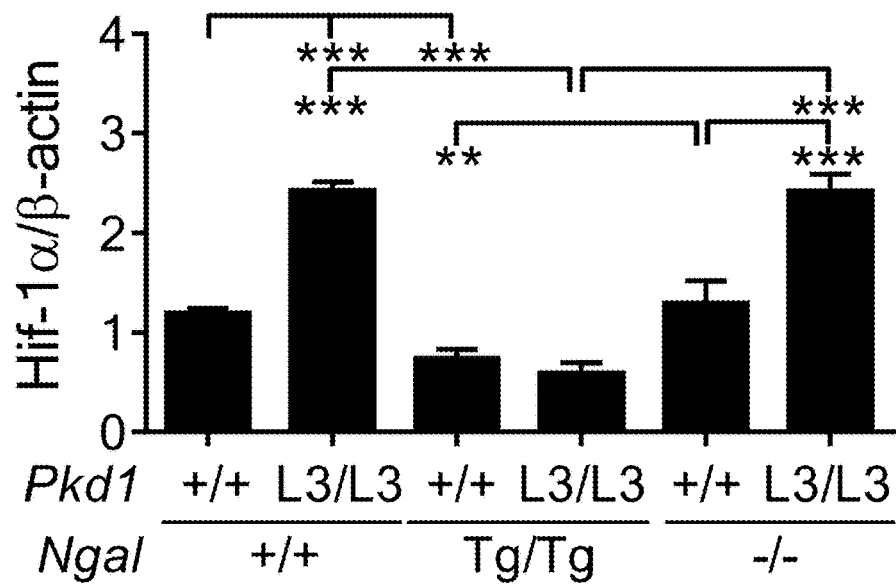

Overexpression of Cdh16-mNgal Reduces Interstitial Fibrosis in Pkd1$^{L3/L3}$; Ngal$^{Tg/Tg}$ Mice Hematoxylin and eosin-stained (H&E, FIG. 9A, upper panels) and Masson's trichrome-stained (FIG. 9A, lower panels) kidney sections were examined at 21D. Wild type mice had a significant lower renal fibrosis scores than both Pkd1$^{L3/L3}$ (p=0.002) and Pkd1$^{L3/L3}$; Ngal$^{-/-}$ (p=0.015) mice but not Pkd1$^{L3/L3}$; Ngal$^{Tg/Tg}$ mice (p=0.417) (FIG. 9B). The renal levels of α-SMA and HIF-1α, the molecules associated with progressive fibrosis of PKD were further examined. Western-blot analyses demonstrated that the levels of α-SMA in Pkd1$^{L3/L3}$; Ngal$^{Tg/Tg}$ mice was comparable to those of wild type mice (FIG. 9C); however, the expression of α-SMA and HIF-1α were significantly lower than those of other two kind of PKD mice (both p<0.001 versus Pkd1$^{L3/L3}$; Ngal$^{Tg/Tg}$) (FIGS. 9D and 9E). Thus, the expressions of α-SMA and HIF-la in these mice were highly correlated with their fibrotic score.

Figure 10A:
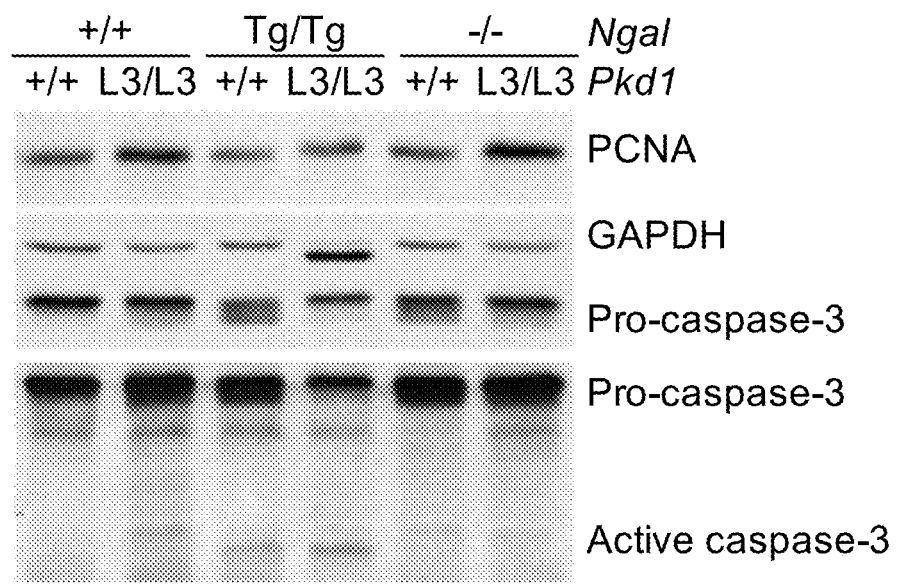
FIGS. 10A-10C show that the overexpression of exogenous kidney-specific NGAL reduces the renal levels of PCNA and pro-caspase-3 of $Pkd1^{L3/L3}$ mice: <FIG. 10A> representative Western blotting results of PCNA, caspase-3, and Glyceraldehyde 3-phosphate dehydrogenase (GAPDH, loading control) at 21D in the different genotypes; <FIG. 10B> quantification of Western blotting results for PCNA/GAPDH; <FIG. 10C> quantification of Western blotting results for pro-caspase-3/GAPDH, in which bar charts show means±SEM of three samples; p<0.01; *p<0.001.
Figure 10B:
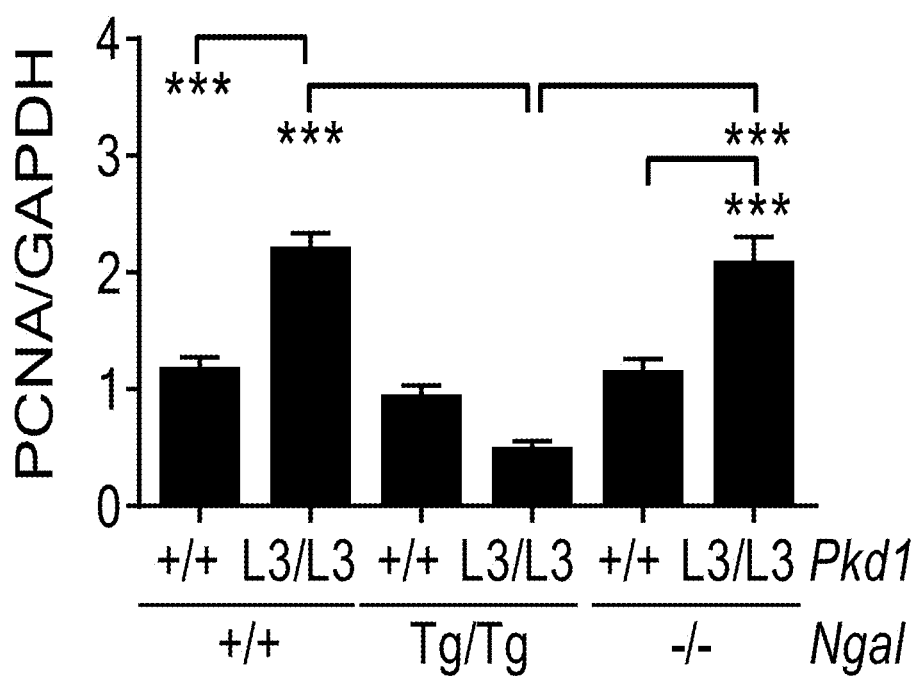
Figure 10C:
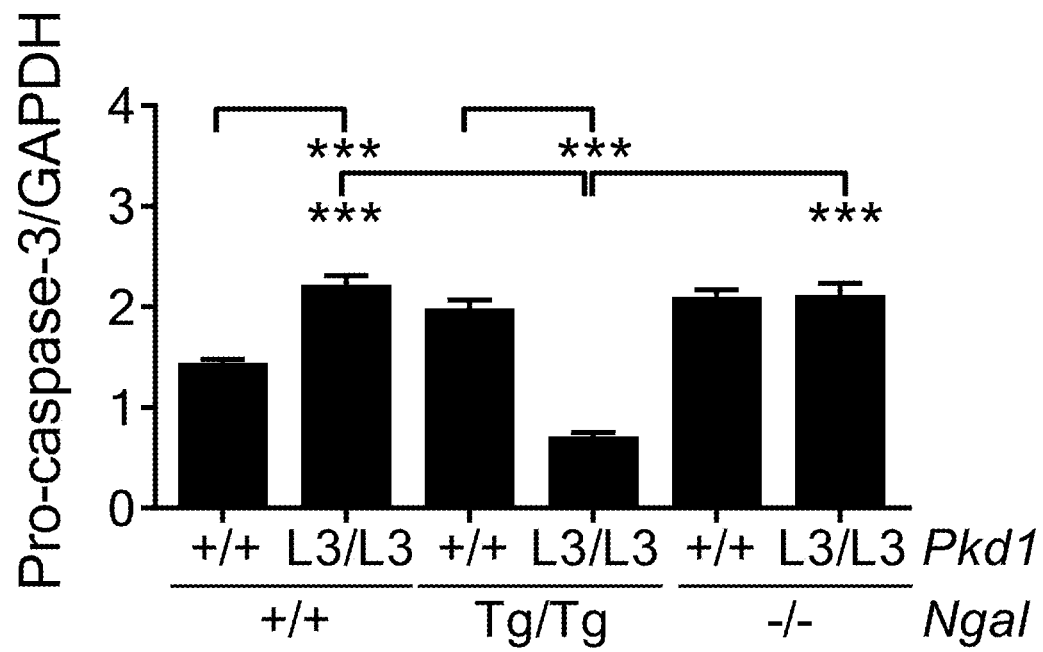

The Changes of Proliferating Cell Nuclear Antigen (PCNA), and Caspase-3 in Pkd1$^{L3/L3}$; Ngal$^{Tg/Tg}$ Mice Both proliferation and apoptosis were increased in early cystic formation of polycystic kidneys. Western-blot analyses (FIG. 10A) revealed that both the expression of pro-caspase-3 and PCNA were reduced and that active caspase-3 increased in Pkd1$^{L3/L3}$; Ngal$^{Tg/Tg}$ mice as compared to other two kinds of PKD mice (both p<0.001 versus Pkd1$^{L3/L3}$; Ngal$^{Tg/Tg}$) (FIGS. 10B and 10C).

Figure 11A:
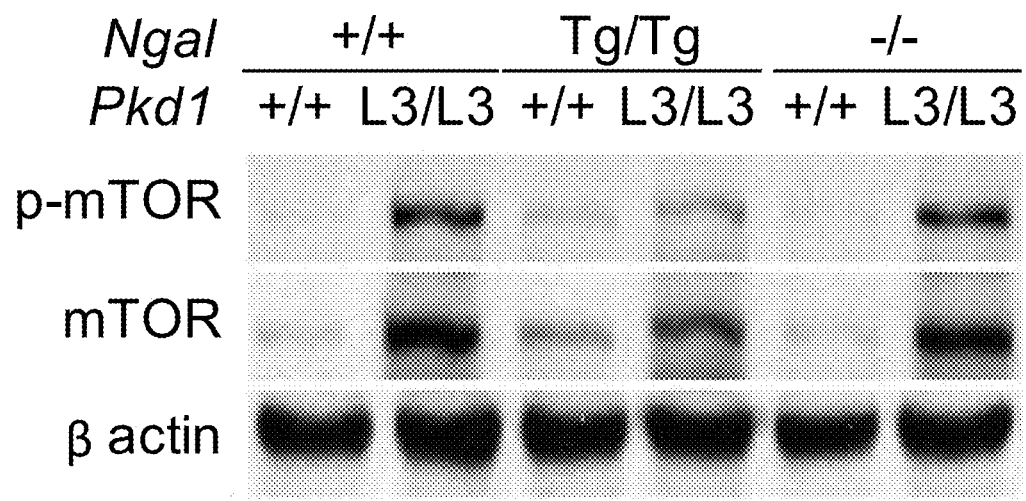
FIGS. 11A-11C show that the overexpression of exogenous kidney-specific NGAL reduces the levels of phospho-mTOR (p-mTOR) and mTOR of $Pkd1^{L3/L3}$ mice: <FIG. 11A> representative Western blotting results of phospho-mTOR (Ser2448), mTOR, and β-actin (loading control) at 21D in the different genotypes; <FIGS. 11B and 11C> quantification of Western blotting results for phospho-mTOR/β-actin, and mTOR/β-actin, respectively, in which bar charts show the means±SEM of three samples; *p<0.05; p<0.01; *p<0.001.
Figure 11B:
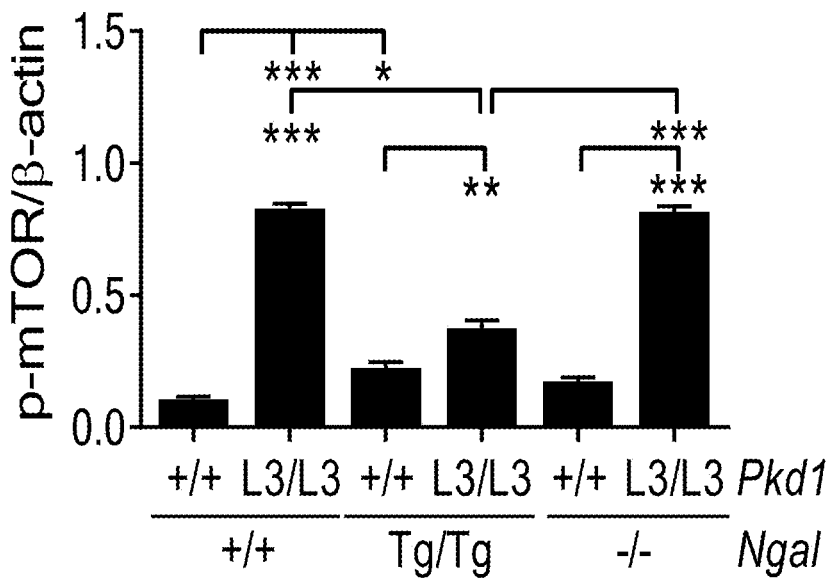
Figure 11C:
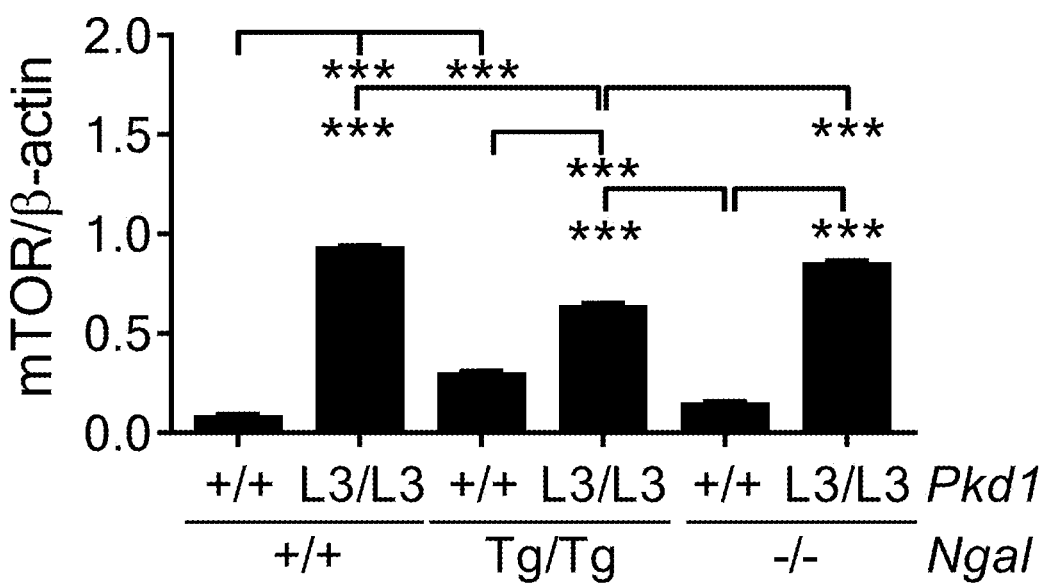
Figure 12A:
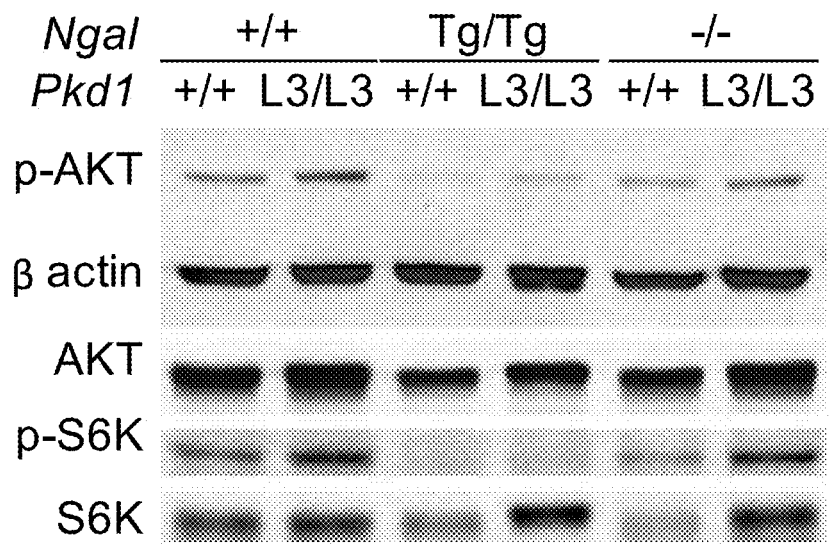
FIGS. 12A-12C show that the overexpression of exogenous kidney-specific NGAL reduces the renal levels of phospho-Akt, Akt, phospho-S6K and S6K of $Pkd1^{L3/L3}$ mice: <FIG. 12A> representative Western blotting results of phospho-Akt (Ser473), Akt, phospho-S6K (Thr389), S6K and β-actin (loading control) at 21D in the different genotypes; <FIGS. 12B and 12C> quantification of Western blotting results for phospho-Akt/β-actin and phospho-S6K/β-actin, respectively, in which bar charts show means±SEM of three samples; *p<0.05; p<0.01; *p<0.001.
Figure 12B:
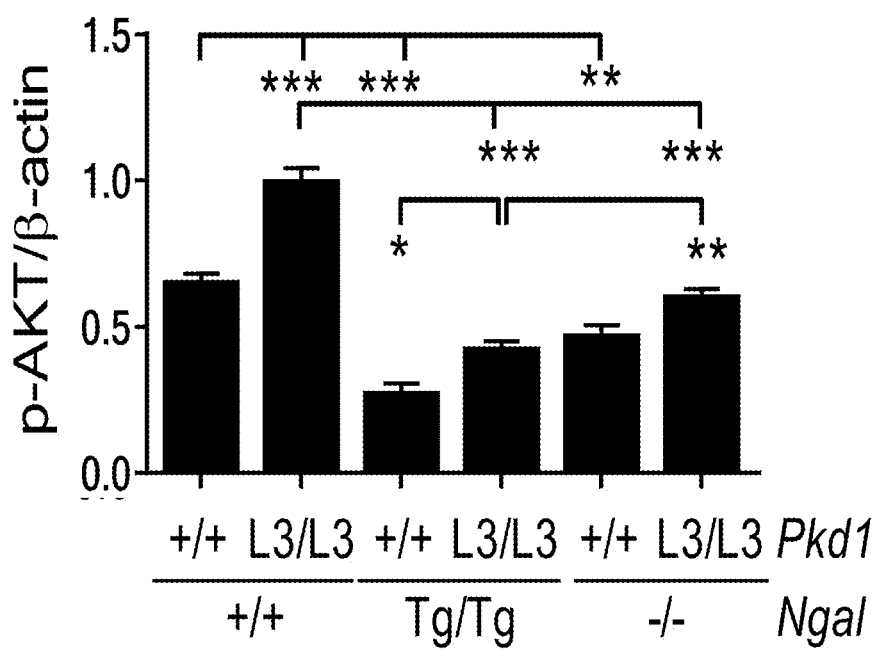
Figure 12C:
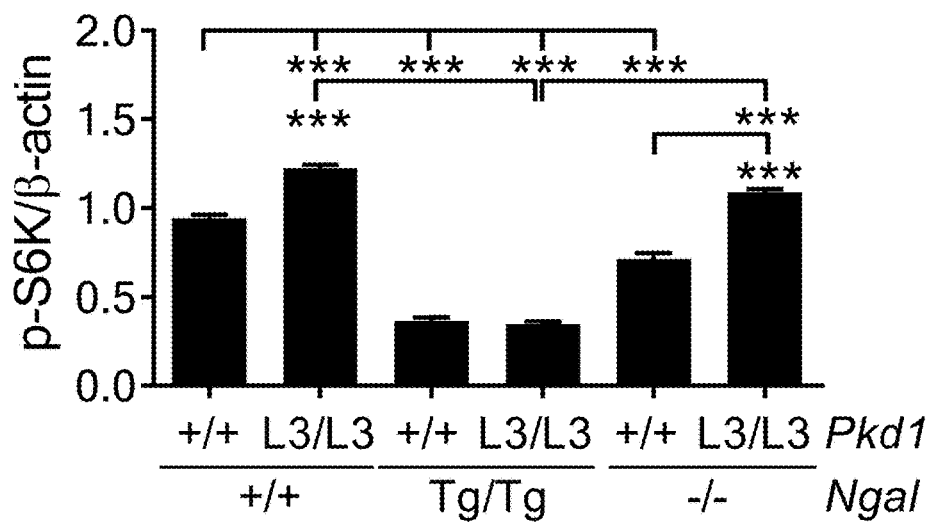

Renal Level of Mammalian Target of Rapamycin (mTOR) is Decreased in Pkd1$^{L3/L3}$; Ngal$^{Tg/Tg}$ Mice with Downregulation of Akt and S6 Kinase Signaling All of the three PKD mice exhibited increased expressions of mTOR and p-mTOR as compared to their respective control littermates without PKD (FIG. 11A). Additionally, Pkd1$^{L3/L3}$; Ngal$^{Tg/Tg}$ mice had the lowest mTOR and p-mTOR levels compared to Pkd1$^{L3/L3}$ and Pkd1$^{L3/L3}$; Ngal$^{-/-}$ mice (both p<0.001 versus Pkd1$^{L3/L3}$; Ngal$^{Tg/Tg}$) (FIGS. 11B-11C). A major upstream regulator (Akt) and a downstream target [ribosomal protein S6 Kinase (S6K)] of mTOR are involved in cell proliferation. Subsequent Western-blot analyses (FIG. 12A) confirmed that the expression of phosphorylated Akt (p-Akt) and phosphorylated S6K (p-S6K) were significantly reduced in Pkd1$^{L3/L3}$; Ngal$^{Tg/Tg}$ mice as compared to the other two kinds of PKD mice (both p<0.001 versus Pkd1$^{L3/L3}$; Ngal$^{Tg/Tg}$) (FIGS. 12B and 12C).

Figure 13A:
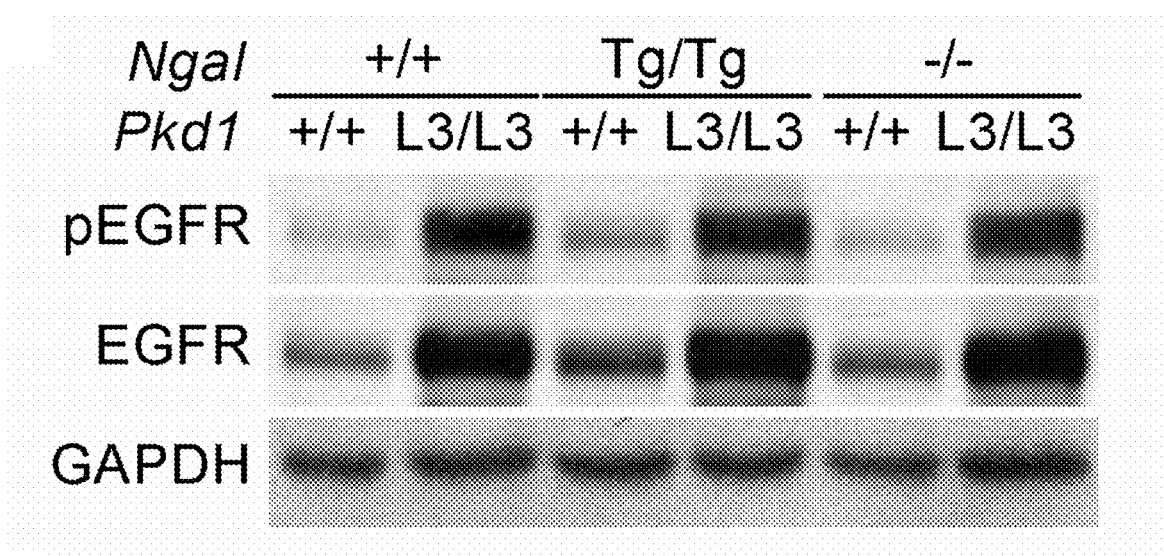
FIGS. 13A-13C show that the renal levels of phospho-EGFR and EGFR are greater in $Pkd1^{L3/L3}$, $Ngal^{Tg/Tg}$, $Pkd1^{L3/L3}$ and $Pkd1^{L3/L3}$; $Ngal^{-/-}$ mice: <FIG. 13A> representative Western blotting results of phospho-EGFR (Tyr1068), EGFR and GAPDH (loading control) at 21D in the different genotypes; <FIGS. 13B and 13C> quantification of Western blotting results for phospho-EGFR/GAPDH, and EGFR/GAPDH, respectively, in which bar charts show the means±SEM of three samples; p<0.01; *p<0.001.
Figure 13B:
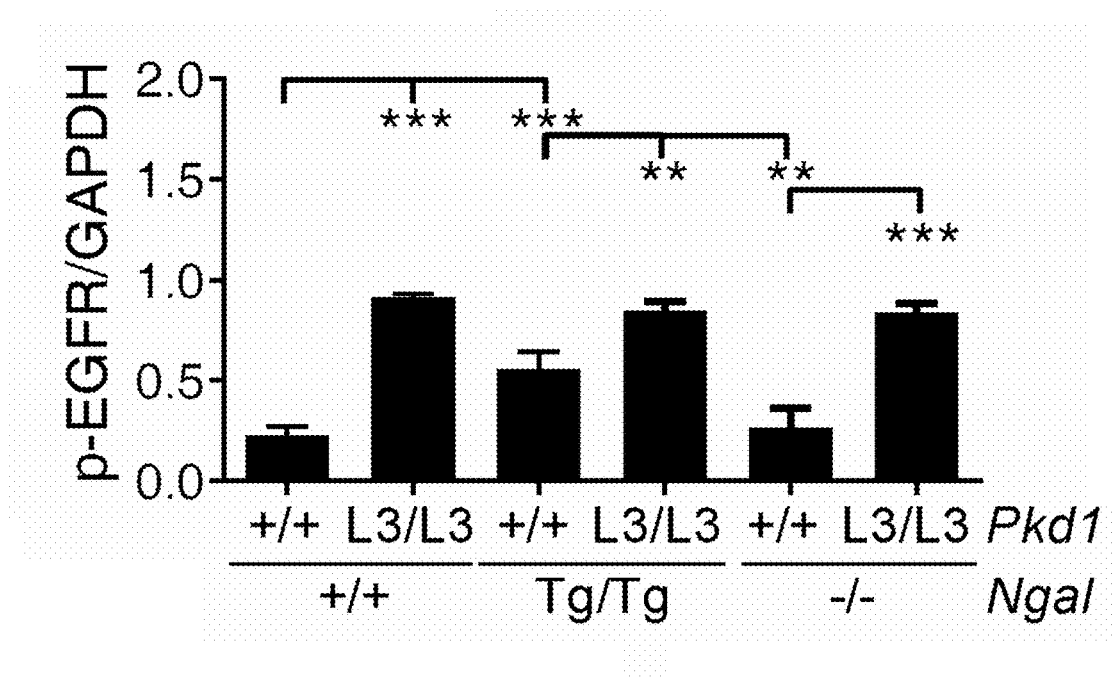
Figure 13C:
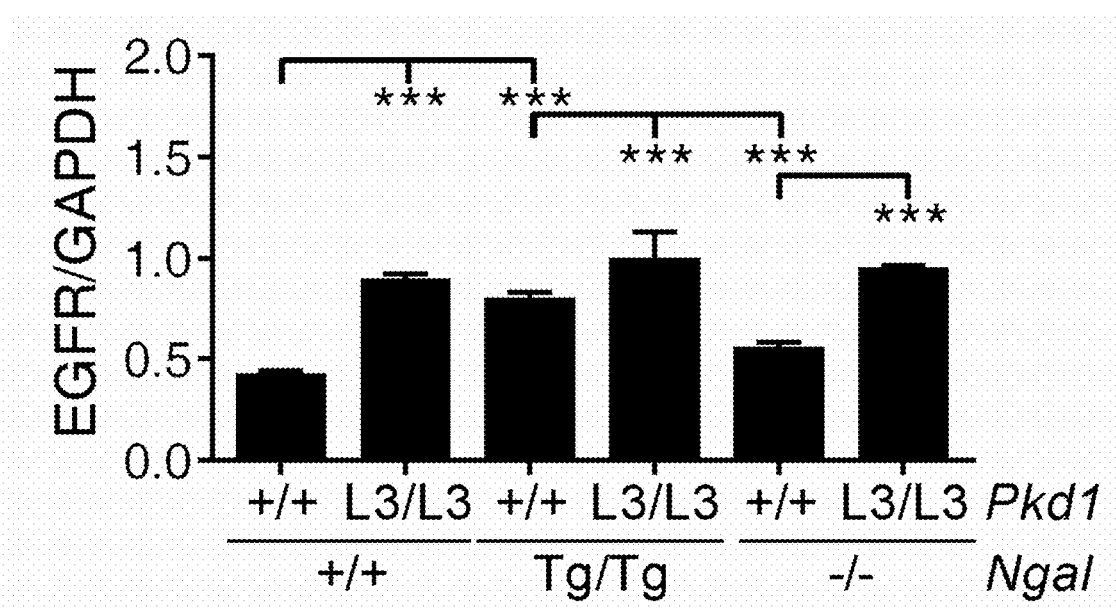

Renal Levels of Epidermal Growth Factor Receptor (EGFR) and Phosphorylated EGFR (p-EGFR) in Pkd1$^{L3/L3}$; Ngal$^{Tg/Tg}$ Mice Overexpression and apical mislocation of EGFR and p-EGFR is known to promote cyst growth, and inhibition of EGFR tyrosine kinase activity can attenuate the development of PKD (Orellana S A, et al., *Kidney Int*, 47: 490-499, 1995; Du J, et al., *Am J Physiol*, 269: C487-495, 1995; Sweeney W E, et al., *Kidney Int*, 57: 33-40, 2000; Tones V E, et al., *Kidney Int*, 64: 1573-1579, 2003). Western-blot analyses (FIG. 13A) demonstrated that the expression of both EGFR and p-EGFR (Tyr1068) were significantly increased in these three PKD mice as compared with their control littermates without PKD (p<0.001 versus control) (FIGS. 13B and 13C). However, the ratio of p-EGFR/EGFR revealed no difference among the three PKD mice.

Preparation of Recombinant Mouse Ngal Protein (mNGAL) and Treatment PKD Mice

Figure 14A:
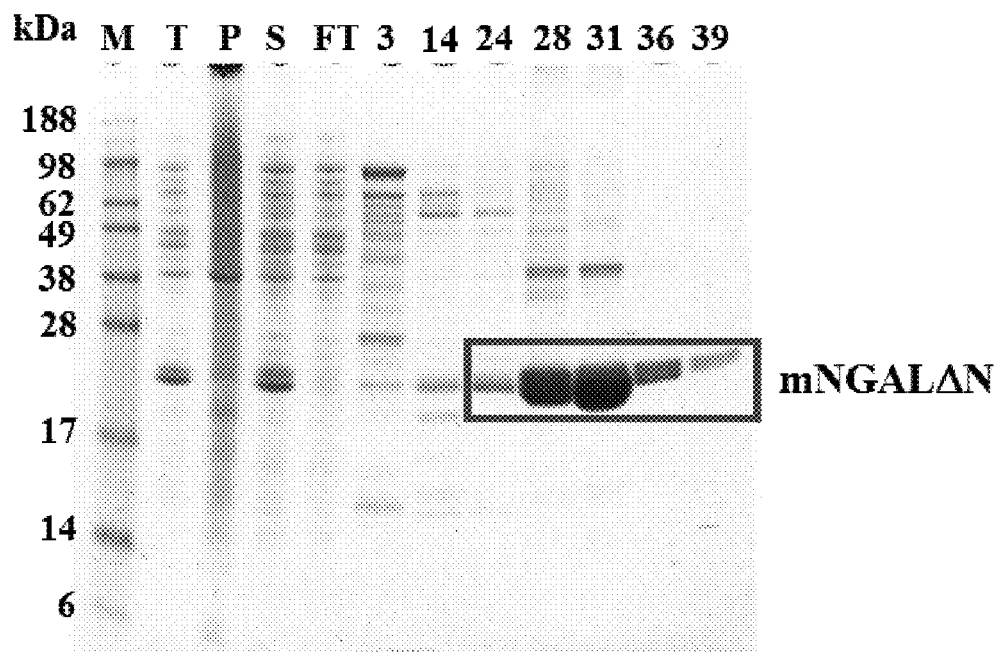
FIGS. 14A-14D show SDS-PAGE of the purified recombinant mNGALΔN (mouse N-terminally truncated NGALA protein) and therapeutic effect of mNGAL-injection: <FIG. 14A> initial purification of recombinant mNGALΔN via $Ni^{2+}$-NTA chromatography; Lane M, protein marker; Lane T, total cell lysate; Lane P, insoluble pellet; Lane S, soluble fraction; Lane FT, flow through; Lane 3-39, eluted fractions; <FIG. 14B> further purification of recombinant mNGALΔN via Q anion exchange chromatography; <FIG. 14C> Kaplan-Meier analysis of survival in $Pkd1^{L3/L3}$ (open triangles), $Pkd1^{L3/L3}$; $Ngal^{Tg/Tg}$ (filled circles), $Pkd1^{L3/L3}$; $Ngal^{-/-}$ (open squares), mNGAL-injected $Pkd1^{L3/L3}$ (filled triangles) and mNGAL-injected $Pkd1^{L3/L3}$; $Ngal^{-/-}$ mice (filled squares); <FIG. 14D> representative images of the kidneys of untreated $Pkd1^{L3/L3}$ (a-b), and mNGAL-treated $Pkd1^{L3/L3}$ mice (c-d).
Figure 14B:
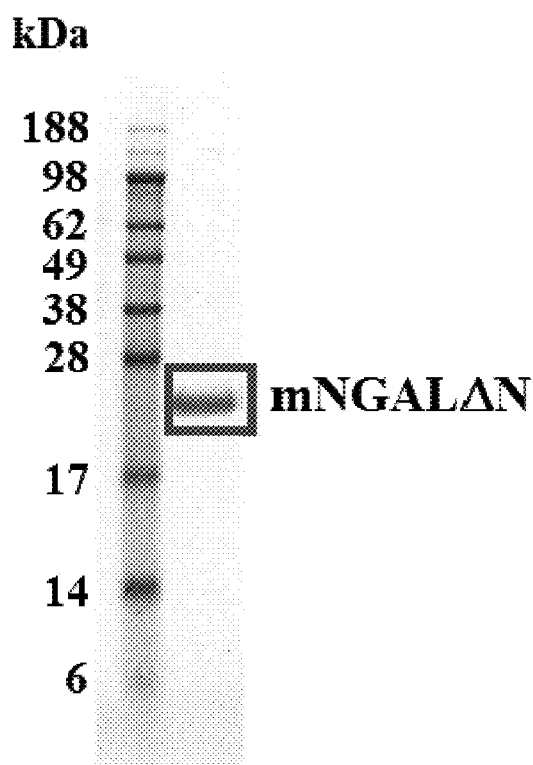
Figure 14C:
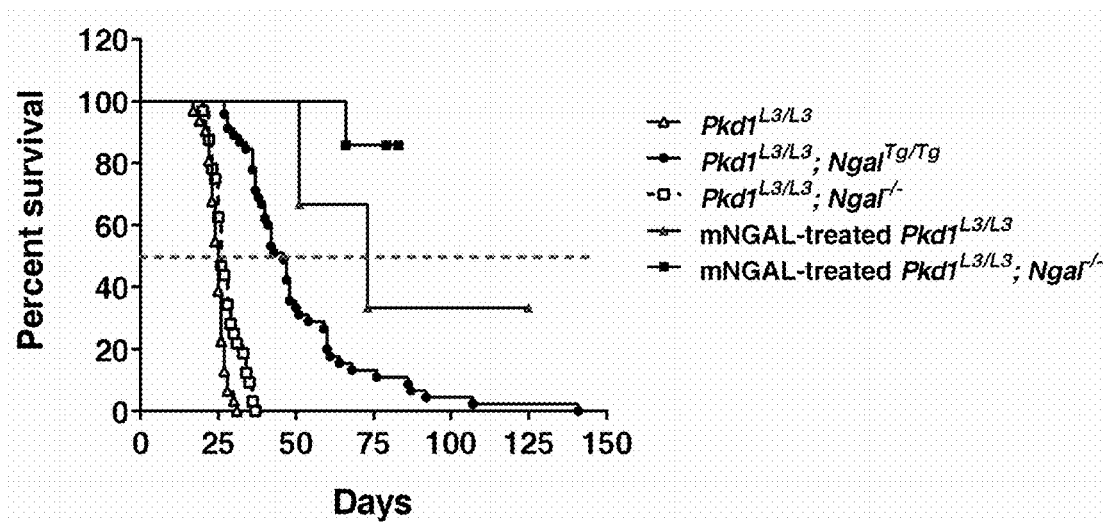
Figure 14D:
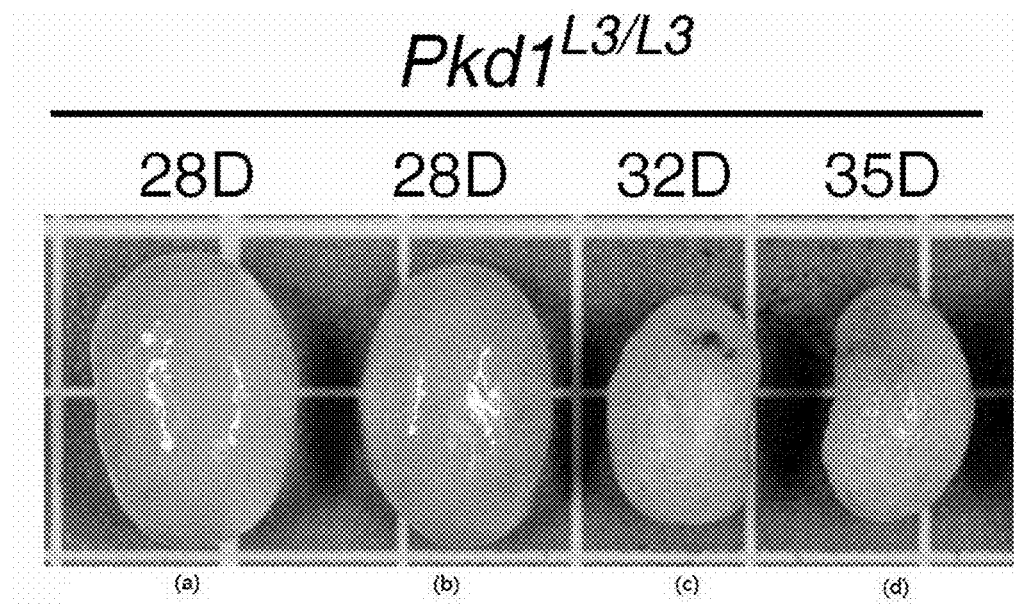

In our study, we emphasized the therapeutic effect of secretory Ngal on a reduction of cyst growth. We further prepared the recombinant mouse Ngal protein (mNGAL), and then performed intraperitoneal injection of functional recombinant mNgal protein with low endotoxin and high purity (100 µg/day) into the PKD mice. The coding sequences of mNGAL (residues from 23 to 200) was subcloned into pET21a vector with an N-terminal His$_6$-tag to facilitate purification. The correct construct by sequencing was subsequently transformed to *E. coli* BL21 (DE3) for protein expression. The 60 ml overnight culture of a single transformant was used to inoculate 6 liters of fresh LB medium containing 100 µg/ml ampicillin. The cells were grown to A600 nm=0.6~1.0 and induced with 0.5 mM isopropyl β-thiogalactopyranoside (IPTG) at 20° C. After 16 hr, the cells were harvested by centrifugation at 7,000×g for 15 mM to collect the cell paste. The cell pellet was resuspended immediately in the lysis buffer containing 20 mM Tris-HCl, 400 mM NaCl, 10 mM imidazole, pH 8.0. The cell suspension was disrupted by Constant Cell Disruption System (CONSTANT SYSTEM Ltd., UK) and centrifuged at 17,000×g to remove cell debris. The cell-free extract was loaded onto a Ni$^{2+}$-NTA column, which had been previously equilibrated with lysis buffer. The column was washed with lysis buffer, subsequently the His$_6$-tagged mNGAL was eluted by a linear gradient from 10 mM to 500 mM imidazole (FIG. 14A). The purified His$_6$-tagged mNGAL was diluted with four-fold 20 mM Tris, pH 8.0 buffer and subsequently was loaded onto a Q anion exchange column, which had been previously equilibrated with 20 mM Tris, pH 8.0 buffer. The low lipopolysaccharides (LPS) containing His$_6$-tagged mNGAL was collected from the flow through of Q anion exchange column (FIG. 14B). Finally the His$_6$-tagged mNGAL was concentrated and exchanged into PBS buffer with 10 kDa cut-off size membrane of Vivaspin 20 (Sartorius, Germany) for storage at −80° C. The Pkd1$^{L3/L3}$ (n=3) and Pkd1$^{L3/L3}$; Ngal$^{-/-}$ mice (n=6) were injected with mNGAL (100 µl/day) after postnatal day 7 via subcutaneous (SC) or intraperitoneal injection (IP). Our data demonstrated that the survival rate was markedly increased in all mNGAL-injected Pkd1$^{L3/L3}$ and Pkd1$^{L3/L3}$; Ngal$^{-/-}$ mice as compared with untreated group (FIG. 14C). The cystic kidneys of Pkd1$^{L3/L3}$ mice was also significantly retarded in mNGAL-treated Pkd1$^{L3/L3}$ mice as compared with untreated group (FIG. 14D and Table 1).

TABLE 1

|  | (a) | (b) | (c) | (d) |
| --- | --- | --- | --- | --- |
| mNGAL treatment | — | — | + | + |
| Dosage/day | — | — | 100 µg | 100 µg |
| Treatment period | — | — | 12-35D | 9-32D |
| Kidney/body weight ratio (%) | 30.96% | 29.35% | 13.72% | 12.74% |

What is claimed is:

1. A method of preventing polycystic kidney disease (PKD), comprising: administering an effective amount of neutrophil gelatinase-associated lipocalin (NGAL) to a subject in need, wherein preventing PKD is statistically significantly improving survival and lifespan of a patient through at least four of the following pathophysiological mechanisms or features: retarding renal cyst growth, reducing renal cyst volume and kidney/body weight, reducing renal interstitial fibrosis, reducing hypoxia in the interstitial compartment of kidney, increasing apoptosis of cystic epithelial cells and decreasing proliferation of cystic epithelial cells in the kidney;

wherein the PKD is autosomal dominant polycystic kidney disease (ADPKD), and administering the effective amount of neutrophil gelatinase-associated lipocalin (NGAL) is before statistically significant ischemic injury.

2. The method of claim 1, wherein the NGAL induces at least one of the following: increased expression of NGAL and NGAL receptor (NGAL-R), increased active-caspase-3 and decreased pro-caspase 3 in preventing PKD.

3. The method of claim 1, wherein the NGAL inhibits the expression of at least one of: $\alpha$-SMA, collagen, hypoxia-inducible factor 1-$\alpha$ (HIF-1$\alpha$), pro-caspase 3, proliferating cell nuclear antigen (PCNA), Akt, mammalian target of rapamycin (mTOR) and S6K in preventing PKD.

4. The method of claim 1, wherein the NGAL is dose-dependent.

5. The method of claim 1, wherein the NGAL induces at least four of the following: reduced $\alpha$-SMA, reduced hypoxia-inducible factor 1-$\alpha$ (HIF-1$\alpha$), reduced Akt, reduced mammalian target of rapamycin (mTOR), reduced S6K, reduced pro-caspase 3, reduced proliferating cell nuclear antigen (PCNA), increased expression of NGAL and NGAL receptor (NGAL-R), and increased active-caspase-3 in preventing PKD.

\* \* \* \* \*

SEQUENCE LISTING

<160> NUMBER OF SEQ ID NOS: 7

<210> SEQ ID NO 1
<211> LENGTH: 22

<212> TYPE: DNA
<213> ORGANISM: Artificial Sequence
<220> FEATURE:
<223> OTHER INFORMATION: Primer

<400> SEQUENCE: 1
atggccctga gtgtcatgtg tc                                    22

<210> SEQ ID NO 2
<211> LENGTH: 22
<212> TYPE: DNA
<213> ORGANISM: Artificial Sequence
<220> FEATURE:
<223> OTHER INFORMATION: Primer

<400> SEQUENCE: 2
gctccagatg ctccttggta tg                                    22

<210> SEQ ID NO 3
<211> LENGTH: 22
<212> TYPE: DNA
<213> ORGANISM: Artificial Sequence
<220> FEATURE:
<223> OTHER INFORMATION: Primer

<400> SEQUENCE: 3
ggcattgtta ccaactggga cg                                    22

<210> SEQ ID NO 4
<211> LENGTH: 20
<212> TYPE: DNA
<213> ORGANISM: Artificial Sequence
<220> FEATURE:
<223> OTHER INFORMATION: Primer

<400> SEQUENCE: 4
aggaaggctg gaaaagagcc                                       20

<210> SEQ ID NO 5
<211> LENGTH: 24
<212> TYPE: DNA
<213> ORGANISM: Artificial Sequence
<220> FEATURE:
<223> OTHER INFORMATION: Primer

<400> SEQUENCE: 5
ttcctcctcc agcacacatc agac                                  24

<210> SEQ ID NO 6
<211> LENGTH: 23
<212> TYPE: DNA
<213> ORGANISM: Artificial Sequence
<220> FEATURE:
<223> OTHER INFORMATION: Primer

<400> SEQUENCE: 6
gagtaacaac ccgtcggatt ctc                                   23

<210> SEQ ID NO 7
<211> LENGTH: 25
<212> TYPE: DNA
<213> ORGANISM: Artificial Sequence

```
<220> FEATURE:
<223> OTHER INFORMATION: Primer

<400> SEQUENCE: 7
aggggttact gtcagagtgg ctatc                                                 25
```